(12) United States Patent
Caputo et al.

(10) Patent No.: US 6,747,159 B2
(45) Date of Patent: Jun. 8, 2004

(54) SYMMETRIC, MONOFUNCTIONALISED POLYMETHINE DYES LABELLING REAGENTS

(76) Inventors: Giuseppe Caputo, Via Principe Tommaso 21, I-10125 Turin (IT); Leopoldo Della Ciana, Via Torino 475, I-10015 Turin (IT)

(*) Notice: Subject to any disclaimer, the term of this patent is extended or adjusted under 35 U.S.C. 154(b) by 4 days.

(21) Appl. No.: 10/038,554

(22) Filed: Jan. 2, 2002

(65) Prior Publication Data

US 2002/0156288 A1 Oct. 24, 2002

(30) Foreign Application Priority Data

Jan. 3, 2001 (EP) .............................................. 01100260

(51) Int. Cl.[7] ...................... C07D 403/06; C07D 403/08
(52) U.S. Cl. ........................................ 548/414; 548/455
(58) Field of Search .................................. 548/414, 455

(56) References Cited

U.S. PATENT DOCUMENTS

| | | | |
|---|---|---|---|
| 3,282,932 A | 11/1966 | Lincoln et al. | 260/240.4 |
| 3,397,981 A | 8/1968 | Lincoln et al. | 96/102 |
| 3,403,026 A | 9/1968 | Oliver et al. | 96/105 |
| 3,408,195 A | 10/1968 | Oliver | 96/105 |
| 3,656,960 A | 4/1972 | Oliver | 96/124 |
| 4,981,977 A | 1/1991 | Southwick et al. | 548/455 |
| 5,268,486 A | 12/1993 | Waggoner et al. | 548/427 |
| 5,519,145 A * | 5/1996 | Fabricius et al. | 548/450 |
| 5,627,027 A | 5/1997 | Waggoner | 435/6 |
| 6,002,003 A | 12/1999 | Shen et al. | 544/232 |
| 6,027,709 A | 2/2000 | Little et al. | 424/1.65 |
| 6,593,148 B1 * | 7/2003 | Narayanan | 436/546 |

FOREIGN PATENT DOCUMENTS

| | | | |
|---|---|---|---|
| CA | 2315207 A1 * | 6/1999 | |
| DE | 199 11 102 A1 | 9/2000 | C09B/62/36 |
| EP | 0 670 374 A1 | 9/1995 | C12Q/1/68 |
| EP | 0 753 584 A1 | 1/1997 | C12Q/1/68 |
| GB | 640127 | 7/1950 | |
| JP | 06145539 | 5/1994 | C09B/23/00 |
| JP | 11-286498 A * | 10/1999 | |
| WO | WO-96/35696 A1 * | 11/1996 | |
| WO | WO 99/31181 | 6/1999 | C09B/23/06 |
| WO | WO-02/38190 A2 * | 5/2002 | |

OTHER PUBLICATIONS

CAS Registry No. 179028–63–3 (Aug. 2, 1996).*
CAS Registry No. 173536–26–0 (Feb. 27, 1996).*
Gallaher et al., Anal. Chem., 2000, 72(9), pp. 2080–2086.*
Gallaher et al., Analyst (Cambridge, United Kingdom) (1999), 124(11), pp. 1541–1546.*
Flanagan, Jr., Bioconjugate Chemistry (1997), 8(5), pp. 751–756.*
An English translation of JP 06–145539, 1994.*
Lipowska et al. Synthetic Communications (1993), 23(21), pp. 3087–3094.*

Babichev et al.; "Benzothiazolylalkyl Carbinols" translated from *Zhurnal Obshchei Khimii* 32:3 850–857 (1962).
Babichev; "Condensation of 0–Aminobenzenethiol with Lactones" translated from *Zhurnal Obshchei Khimii* 33:9 2942–2948 (1963).
Brooker; "Chapter 11—Sensitizing and Desensitizing Dyes" *The Theory of the Photographic Process* 198–232, year not available.
Dähne; "Spectral Sensitization and Electronic Structure of Organic Dyes" *Photographic Science and Engineering* 23:4 219–239 (1979).
Dieckmann et al.; "Ueber Chlormalonaldehyd, [2–Chlorpropen (2)–ol(3)–al(1)]"*Berichte* 4638–4639 (1904).
Fry; "Chapter 15—Cyanine Dyes and Related Compounds" *Rodd's Chemistry of Carbon Compounds, Second Edition* 4(*b*) 369 (1977).
Fry; "Chapter 15—Cyanine Dyes and Related Compounds" *Supplements to the 2nd Edition of Rodd's Chemistry of Carbon Compounds* 267–268 (1985).
Hamer, "Some Unsymmetrical Pentamethincyanine Dyes" *J. Chem. Soc.* 32 32–37 (1969).
Imasaka et al., "Semiconductor Laser Fluorimetry in the Near–Infrared Region" *Anal. Chem.* 56 1077–1079 (1984).
Imasaka et al.; "Diode Lasers and Practical Trace Analysis" *Analytical Chemistry* 62:6 363A–371A (1990).
Kiprianov; "Influence of the Solvent on the Colour of Dyes (Solvatochromism)"*Russian Chemical Reviews* 29:11 618–626 (1960).

(List continued on next page.)

*Primary Examiner*—Laura L. Stockton
(74) *Attorney, Agent, or Firm*—Myers Bigel Sibley & Sajovec, PA

(57) ABSTRACT

A symmetric cyanine of the formula:

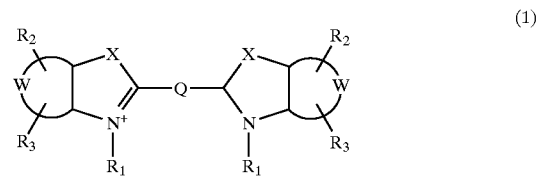

(1)

wherein:

X is selected from the group consisting of O, S and $C(CH_3)_2$;

W represents non-metal atoms required to form a benzo-condensed or a naphto-condensed ring;

$R_1$ is selected from the group consisting of $(CH_2)_nCH_3$, $(CH_2)_nSO_3^-$ and $(CH_2)_nSO_3H$, wherein n is an integer selected from 0 to 6 when $R_1$ is $(CH_2)_nCH_3$, and n is an integer selected from 3 to 6 when $R_1$ is $(CH_2)_nSO_3^-$ or $(CH_2)_nSO_3H$;

$R_2$ and $R_3$ are independently selected from the group consisting of H, a sulphonic moiety and a sulphonate moiety and Q is a substituted polymethine bridge.

4 Claims, No Drawings

OTHER PUBLICATIONS

Kiprianov et al.; "The Colour of Dyes and Steric Hindrance in their Molecules" *Russian Chemical Reviews* 35:5 361–373 (1966).

Kiprianov et al.; "Absorption Spectra of Organic Dyes Containing Two Chromophores" *Russian Chemical Reviews* 40:7 594–607 (1971).

Lindsey et al.; "Visible Light–Harvesting in Covalently–Linked Porphyrin–Cyanine Dyes" *Tetrahedron* 45:15 4845–4866 (1989).

Mank et al.; "Visible Diode Laser Induced Fluorescence Detection in Liquid Chromatography after Percolum Derivatization of Thiols" *Anal. Chem.* 65 2197–2203 (1993).

Mank et al.; "Visible Diode Laser–Induced Fluoroescence Detection in Liquid Chromatography after Percolum Derivitization of Amines" *Anal. Chem.* 67 1742–1748 (1995).

Mikhailenko et al.; "Effect of Polar Substituents and the Length of the Polymethine Chain on the Color of Cyanine Dyes of the Benzo [c,d] Indole Series" translated from *Zhurnal Organicheskoi Khimii* 18:2 435–441 (1982).

Mujumdar et al.; "Cyanine Dye Labeling Reagentes Containing Isothiocyanate Groups" *Cytometry* 10 11–19 (1989).

Mujumdar et a. "Cyanine Dye Labeling Reagents" Sulfoindocyanine Succinimidyl Esters *Bioconjugate Chemistry* 4:2 105–111 (1993).

Mujumdar et al.; "Cyanine–Labeling Reagents: Sulfobenzindocyanine Succinimidyl" *Bioconjugate Chem.* 7 356–362 (1996).

Narayanan et al.; "A New Method for the Synthesis of Heptamethine Cyanine Dyes: Synthesis of New Near–Infrared Fluorescent Labels" *J. Org. Chem.* 60 2391–2395 (1995).

Pomogaev et al.; "Meso–Bromo–Substituted Tricarbocyanines with Cyclic–Fragments in the Conjugation Chain" translated from *Zhurnal Organiches koi Khimii* 17:1 (1981), 150–151.

Reynolds et al.; "Stable Heptamethine Pyrylium Dyes that Absorb in the Infrared" *J. Org. Chem.* 42:5 885–888 (1977).

Strekowski et al.; "Facile Derivatizations of Heptamethine Cyanine Dyes" *Synthetic Communications* 22:17 2593–2598 (1992).

Strekowski et al.; "Substitution Reactions of a Nucleofugal Group in Heptamethine Cyanine Dyes. Synthesis of an Isothiocyanato Derivative for Labeling of Proteins with a Near–Infrared Chromophore" *J. Org. Chem.* 57 4578–4580 (1992).

Sturmer et al.; "Table of Contents for Chapter 8—Syntheses and Properties of Cyanine and Related Dyes" *Special Topics in Heterocyclic Chemistry*, 441 (1977).

Yu et al.; "Cyanine dye dUTP analogs for enzymatic labeling of DNA" *Nucleic Acids Research* 22:15 3226–3232 (1994).

Zhu et al.; "Directly labeled DNA probes using fluorescent nucleotides with different length linkers" *Nucleic Acids Research* 22:16 3418–3422 (1994).

Zollinger, "Color Chemistry" 51–69, 361–396 (1987).

Partial European Search Report corresponding to application No. EP 01 10 0260; date of completion: Jul. 26, 2001.

Fry et al.; "Cyanine Dyes and Related Compounds" *Rodd's Chemistry of Carbon Compounds, 2d Ed., Chapter 15* 369–422 (1977).

\* cited by examiner

SYMMETRIC, MONOFUNCTIONALISED POLYMETHINE DYES LABELLING REAGENTS

This application claims priority to European patent application number 01100260.7 filed in English on Jan. 3, 2001 the disclosure of which is hereby incorporated herein by reference.

DESCRIPTION

Polymethine dyes, also known as cyanines, conform to the generalised formula:

$$X-(CR)_n-X^1$$

in which n is an odd positive integer and (n+3) π electrons are distributed over the polymethine chain and the terminal atoms X and $X^1$; R, attached to the methine carbon C, is hydrogen or a radical. In the large majority of dyes X and $X^1$ are the nitrogen atoms in a heterocyclic ring, but dyes are known in which one or both of the groups art non-cyclic or carbocyclic. The —CR— groups can be replaced by one ore more aza (—N═) links.

Comprehensive reviews regarding polymethine dyes have been by written by L. G. S. Brooker, "The Theory of the Photographic Process" Mees Ed., Macmillan, New York, (1942), p. 987 and (1966), p. 198; Frances M. Hamer, in "The Chemistry of Heterocyclic Compounds", Vol 18, "The Cyanine Dyes and Related Compounds", Weissberger, Ed, Wiley Interscience, New York, (1964); G. E. Ficken, "The Chemistry of Synthetic Dyes", Vol 4, K. Venkataraman Ed., Academic Press, New York, (1971), p.211; A. I. Kiprianov, Usp. Khim., 29, 1336, (1960), 35, 361 (1966), 40, 594 (1971); D. W. Heseltine, "The Theory of the Photographic Process",$4^{th}$ edition, James Ed., Macmillan, New York, (1977), chapter 8, "Sensitising and Desensitising Dyes"; S. Daehne, Phot. Sci. Eng., 12, 219 (1979); D. J. Fry, "Rodd's Chemistry of Carbon Compounds", "Cyanine Dyes and Related Compounds", Vol. IVb, chapter 15, p.369 Elsevier, Amsterdam, (1977); Supplement to Vol. IVb, $2^{nd}$ Edition (1985), p.267; H. Zollinger, "Color Chemistry", VCH, Weinheim (1987), chapters 3 and 14; D. M. Sturmer, "The Chemistry of Heterocyclic Compounds", "Special Topics in Heterocyclic Chemistry", chapter VIII, "Synthesis and Properties of Cyanine and Related Dyes", Weissberger Ed., Wiley, New York, (1977); "The Kirk-Othmer Encyclopaedia of Chemical Technology" Vol 7, p. 782, "Cyanine Dyes", Wiley, New-York, (1993).

For many years, polymethine dyes have been very useful as sensitisers in photography, especially in the red and near infrared regions of the spectrum. However, in more recent years, there has been an upsurge of new uses of these dyes in innovative technological areas, such as laser and electro-optic applications, optical recording media, medical, biological and diagnostic. These new applications of polymethine dyes place high demands on the degree of purity required, and the reproducibility of synthetic methods and purification steps is very important. These requirements are especially stringent for dyes designed to improve detection of ribonucleic acid (RNA), deoxyribonucleic acid (DNA) and of antigens in immunoassays. In these fields, the trend toward an increasing miniaturisation is accompanied by an increasing demand on sensitivity of the reporter molecules or labels. One way to increase the sensitivity of conventional fluorescence method is to use laser sources for the excitation. However, traditional fluorescent labels based on fluoresceins or rhodamins required expensive and/or bulky lasers. Moreover, their fluorescence occurs in the blue-green to green regions of the visible spectrum, where interference from the sample matrix is more likely to occur. Polymethine dyes do not suffer from these limitations. They can be efficiently excited by means of small, inexpensive solid state devices such as laser diodes or light emitting diodes, with extinction coefficients often several times higher than fluoresceins and rhodamines; they emit in the red and near-infrared regions of the spectrum, where non-specific fluorescence from the sample is low or lacking; another sources, Raman noise, becomes smaller with the inverse fourth power of wavelength (Imasaka, T., Yoshitake, A., and Ishibashi, N, "Semiconductor Laser Fluorimetry in the Near-Infrared Region", Anal. Chem., 56, 1077 (1984); Imasaka, T., and Ishibashi, N., "Diode Lasers and practical trace Analysis", Anal. Chem., 62, 363 (1990); Matsuoka, M., Ed., "Infrared Absorbing Dyes", Plenum Press, New York, (1990); J. Fabian, H. Nakazumi, M. Matsuoka, "Near-Infrared Absorbing Dyes", Chem. Rev., 92, 1197, (1992); S. Daehne, U. Resch-Genger, O. S. Wolfbeis, "Near-Infrared Dyes for High Technology Applications", Kluwer Academic Publishers, Dordrecht (1997).

To be useful as a label, a dye has to be provided with a suitable side chain containing a functional group. While the main part of the dye structure is generally known from previous applications, the introduction of a functional group into the structure for the purpose of conjugation, or binding to another molecule, represents the innovative step in the inventions concerning the use of the dye as a labelling reagent. In general, only one such functionalised side arm is preferable, in order to avoid cross-linking or purification problems. With a few exceptions, limited to heptamethine dyes, the standard approach in the design of polymethine labelling reagents has been to attach the functionalised side arm to one of the heterocyclic nuclei of the dye, formula (a):

$$HET_1-HET_2-Z$$

See, for instance: J. S. Lindsey, P. A. Brown, and D. A. Siesel, "Visible Light-Harvesting in Covalently-Linked Porphyrin-Cyanine Dyes, Tetrahedron, 45, 4845, (1989); R. B. Mujumdar, L. A. Ernst, S. R. Mujumdar, and A. S. Waggoner, "Cyanine Dye Labelling Reagents Containing Isothiocyanate Groups", Cytometry, 10, 11 (1989); L. A. Ernst, R. K. Gupta, R. B. Mujumdar, and A. S. Waggoner, "Cyanine Dye Labelling Reagents for sulphydryl Groups", Cytometry, 10, 3, (1989); P. L. Southwick P. L., L. A. Ernst, E. W. Tauriello, S. R. Parker, R. B. Mujumdar, S. R. Mujumdar, H. A. Clever, and A. S. Waggoner, "Cyanine Dye Labelling Reagents-Carboxymethylindocyanine Succinimidyl Esters", Cytometry 11, 418 (1990); R. B. Mujumdar, L. A. Ernst, Swati R. Mujumdar, C. J. Lewis, and A. S. Waggoner, "Cyanine Dye Labelling Reagents: Sulfoindocyanine Succinimidyl Esters", Bioconjugate Chemistry, 4, 105, (1993); A. J. G. Mank, E. J. Molenaar, H. Lingeman, C. Goojer, U. A. Th. Brinkman, and N. H. Velthorst, "Visible Diode Laser Induced Fluorescence Detection in Liquid Chromatography after Precolumn Derivatisation of Thiols", Anal. Chem., 65, 2197, (1993); H. Yu., J. Chao, D. Patek, S. R. Mujumdar, and A. S. Waggoner, "Cyanine dye dUTP analogs for enzymatic labelling of DNA Probes", Nucl. Acids Res 22, 3226, (1994); Z. Zho, J. Chao, H. Yu, and A. S. Waggoner, "Directly labelled DNA probes using fluorescent nucleotides with different length linkers", Nucl. Acids, Res, 22, 3226. A. J. G. Mank, H. T. C. van der Laan, , H. Lingeman, Cees Goojer, U. A. Th. Brinkman, and N. H. Velthorst, "Visible Diode Laser-Induced Fluorescence Detection in Liquid Chromatography after Precolumn Derivatisation of Amines", Anal. Chem., 67, 1742, (1995); S. R. Mujumdar, R. B. Mujumdar, C. M. Grant, and A. S. Waggoner, "Cyanine Labelling Reagents: sulfobenzoindocyanine succinimidyl esters", Bioconjugate Chemistry, 7, 356, (1996). Patent Literature: P. L. Southwick, and A. S. Waggoner, "Intermediate for and Fluorescent Cyanine Dyes containing Carboxylic Acid Groups", U.S. Pat. No. 4,981, 977, Jan. 1, 1991; A. S. Waggoner, L. A. Ernst, and Mujumdar, R. B., "Method for Labelling and Detecting Materials Employing Arylsulfonate Cyanine Dyes", U.S. Pat. No. 5,268,486, Dec. 7., 1993; A. S. Waggoner, "Cyanine Dyes as Labelling Reagents for Detection of Biological and Other Materials by Luminescence Methods", U.S. Pat. No. 5,627,027, May 6, 1996; A. S. Waggoner, and R. B. Mujumdar, "Rigidised Trimethine Cyanine Dyes", WO99/311181; G.-Y. Shen, T. S. Dobashi, "Cyanine Dye Activating Group with Improved Coupling Selectivity"; T. S. G. M. Little, R. Raghavachari; N. Narayanan; H. L. Osterman, "Fluorescent Cyanine Dyes", U.S. Pat. No. 6,027,709, Feb. 22, 2000.

The general synthetic strategy necessary to prepare these labelling reagents is as follows. First, a quaternised nitrogen heterocycle $HET_1$ is prepared. Then, this heterocyclic base is reacted with an electrophilic reagent such as PhNH—$(CH=CH)_n$—CH=NHPh.HCl or RO—$(CH=CH)_n$—CH$(OR)_2$, where Ph is a phenyl ring and R a methyl or ethyl group, to obtain a so-called hemicyanine dye, $HET_1$—$(CH=CH)_n$NHPh or $HET_1$—$(CH=CH)_n$NAcPh, where Ac is the acetyl radical, or $HET_1$—$(CH=CH)_n$—OR. These intermediates are then reacted with a different quaternary nitrogen heterocycle, $HET_2$. The functionalised side arm can be attached either to the first or to the second quaternised nitrogen heterocycle. The final result is an asymmetric polymethine labelling reagent, $HET_1$—$(CH=CH)_n$—$HET_2$—Z.

Unfortunately, the hemicyanine intermediates are notoriously difficult to obtain in good yields and/or in a pure form (see, for example, F. M. Hamer, "Some Unsymmetrical Pentamethincyanine Dyes and their Tetramethin Intermediates", J. Chem. Soc., 32 (1949) and R. B. Mujumdar, L. A. Ernst, Swati R. Mujumdar, C. J. Lewis, and A. S. Waggoner, "Cyanine Dye Labelling Reagents: Sulfoindocyanine Succinimidyl Esters", Bioconjugate Chemistry, 4, 105, (1993); in particular, note that when Mank (Anal. Chem., 67, 1744) tried to synthesise an asymmetric dicarbocyanine label described in the previous reference he obtained a total yield of 18% of dicarbocyanines, from which the desired product was difficult to separate; therefore he devised an alternative approach based on 1,3, 3-trimethoxypropene. Unfortunately, this chemical is no longer available commercially.

In order to avoid such difficulties, the present invention is based on an alternative approach to the design of polymethine dyes with a single functionalised side arm. This general approach is illustrated in formula (b), below:

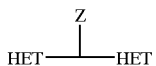

In this case, the functionalised side arm Z is attached to the centre of the dye molecule, resulting in a symmetric labelling reagent. It is immediately obvious from this scheme that only one type of heterocyclic base, HET, is necessary and that the dye can be synthesised in one step, from HET (2 equivalents) and an electrophilic reagent bearing the functionalised side arm. The overall result is a much more convergent, more efficient synthesis of the required labels.

However, thus far, this approach has only found very limited application: the main example is in the synthesis of an isothiocyanate derivative of an heptamethine dye: L. Strekowski, M. Lipowska, and G. Patonay, "Facile Derivatisation of Heptamethine Cyanine Dyes", Synth. Comm., 22(17), 2593–2598 (1992); L. Strekowski, M. Lipowska, and G. Patonay, "Substitution Reactions of a Nucleofugal Group in Heptamethine Cyanine Dyes. Synthesis of an Isothiocyanate Derivative for Labelling of Proteins with a Near-Infrared Chromophore" J. Org. Chem. 57, 4578, (1992); N. Narayan, and G. Patonay, "A New Method for the Synthesis of Heptamethine Cyanine Dyes", J. Org. Chem. 60, 2391–2395, (1995). No example was given in the case of pentamethine labelling reagents and only one example for their trimethine analogues (Compound IX in WO99/311181).

The present inventors succeeded in synthesising symmetric monofunctionalised polymethine dyes as shown in formula (b) having a wide variety of functional groups other than isothiocyanates and also having different functionalised arm chain lengths, which can be used for the labelling of a wide range of analytically and diagnostically useful biomolecules.

Examples of such analytically and diagnostically useful biomolecules include, but are not limited to, nucleotides and nucleosides, oligonucleotides, vitamins, proteins such as for example antibodies, antigens, streptavidin, and the like.

DETAILED DESCRIPTION OF THE INVENTION

The dyes of the present invention are obtained by reacting 2 moles of quaternised nitrogen heterocycle base, HET, with suitable electrophilic reagents, such as diphenylformamidines or trialkylorthoformates and their vinilogs. The functionalised side arm can either be attached to the electrophilic reagent in a previous step, or after the formation of the polymethine dye structure.

The quaternised heterocyclic nuclei, HET, are commercially available, or can be synthesised by known methods from commercially available precursors. For example, the following heterocycle bases are all commercially available: 2,3,3-trimethyl-3-H-indole, 1,1,2-trimethyl-1-H-benz(e) indole, 2-methylbenzothiazole, 2-methylbenzoxazole,2-methylnaphth[1,2-d]thiazole, 2-methylnaphth[1,2-d]oxazole, 2-methyl-naphth[2,1-d]oxazole.

Other heterocyclic nuclei can be synthesised by known methods. For example, sulphonated indoles can be made from the corresponding aminosulphonic acids: these compounds are first converted to the corresponding hydrazinosulphonic acids by diazotisation followed by reduction with tin (II) chloride or other reducing agents, especially $SO_2$ and sulphites; in the next step the hydrazine intermediates were condensed with 2-methylbutanone to yield the corresponding indoles, and then alkylated at the nitrogen with alkyl halides or sultones. Sulphonated benzo- and naphthoxazoles were obtained from the corresponding aminophenol and aminonaphtolsulphonic acids by condensation with acetic anhydride. A similar approach was used to prepare sulphonated benzo- and naphthothiazoles. 2-methyl-naphth[2,1-d] thiazole, was similarly prepared by condensation with acetic anhydride.

N, α-alkylene cyclammonium salts of 3,3-dimethyl-3-H-indole, 1,1,2-dimethyl-1-H-benz(e)indole and their sulphonated analogues, were obtained by following the methods disclosed by L. L. Lincoln and D. W. Heseltine in "Merocyanine Sensitisers for Silver Halide", U.S. Pat. No. 3,282,932 (1966), L. L. Lincoln and L. G. S. Brooker in "Photographic Sensitising Dyes of the Merocyanine And Styryl Types in Silver Halide Photographic Emulsions", U.S. Pat. No. 3,397,981 (1968); G. L. Oliver in "Photographic Silver Halide Emulsions Containing N, α-alkylene Bridged Merocyanine Sensitising Dyes", U.S. Pat. No. 3,403,026 (1968); G. L. Oliver, in "Silver Halide Emulsions Containing N, α-alkylene Bridged Indocyanine Sensitising Dyes", U.S. Pat. No. 3,408,195 (1968). N, α-alkylene cyclammonium salts of benzothiazole, benzoxazole, naphth[1,2-d]thiazole, naphth[2,1-d]oxazole, naphth[1,2-d]oxazole, naphth[2,1-d]oxazole, and their sulphonated analogs were prepared according to the methods described by F. DS. Babichev, and N. Ya Derkach, Ukr. Khim. Zh., 22, 208 (1956); F. S. Babichev, and Neplyuev, "Benzothiazolylalkyl Carboxylic Acids and their Derivatives-IV-Benzothiazolylalkyl Carbinols", Zh. Obsch. Khim., 32, 857 (1962);); F. S. Babichev, and Neplyuev, "Benzothiazolylalkyl Carboxylic Acids and their Derivatives—V-2,3-Polymethylenebenzothiazolium Salts", Zh. Obsch. Khim., 32, 860(1962); F. S. Babichev "Condensation of o-Aminobenzenethiol with Lactones", Zh. Obsch. Khim., 33, 3016, (1963).

Methods for the synthesis of 1-Alkyl-2-methyl-benzo[c,d]indole nuclei, were provided by Ya. B. Shteinberg, in the article "Benzo[c,d]indocyanines", Khim. Geterotsik. Soedin. 3, 340 (1973) and by F. A. Mikhailenko, N. P. Vasilenko, A. D. Kachkovskii and Yu. I. Rozhinskii in "Effect of Polar Substituents and the Length of the Polymethine Chain on the Color of Cyanine Dyes of the Benzo[c,d]indole Series", Zh. Org. Khim., 18, 435 (1982).

In the assembly of the dyes of this invention, two identical molecules of the above described quaternised nitrogen heterocycles are condensed with one molecule of electrophilic intermediates, which provide the bridging methine carbon atoms. For example, N,N-diphenylformamidines or trialkylorthoformates each add one methine carbon atom to the polymethine chain, giving rise to trimethincyanines or carbocyanines; malonaldehyde dianils or trialkoxypropenes contribute three methines to pentamethincyanines, or dicarbocyanines; and glutaconaldehyde dianils introduce five methines, to produce heptamethincyanines or tricarbocyanines, and so on. In one aspect of this invention, the functionalised side arm needed for linking the dye to another molecule, can be inserted into the middle, or meso ($\mu$), position of the polymethine chain either before, or after the synthesis of the cyanine skeleton. Especially useful for this purpose are certain electrophilic reagents bearing a halogen atoms at the meso position, or cyanine dyes with halogens attached at this position. For example, mesochloro- or bromomalonaldehyde dianils can be made from mucochloric or mucobromic acids by treatment with ethanol and aniline hydrochloride according to the directions given in Dieckman and Platz, Berichte 4639 (1904). These compounds can be used to synthesise the corresponding mesochloro, or bromodicarbocyanines. Similarly, the Vilsmeier-Haack-Arnold reaction can be used to prepare cyclic analogs of glutaconaldehyde bearing a halogen atom in the meso position: this structure is then incorporated into the corresponding cyanine dye. For example, S. M. Makin, L. I. Boiko and O. A. Shavrygina describe the synthesis of (5-phenylamino-2,4-trimethylene-3-chloro-2,4-pentadienylidene)phenylammonium chloride from cyclohexanone and the complex formed by mixing N,N-dimethylformamide and phosphorus oxychloride, "Aminoformylation of Unsaturated Aldehydes, 2-Alkoxyaldehydes and their Acetals, and Ketones of the Alicyclic Series", Zh. Org. Khim., 13, 1189 (1977). In our hands, the corresponding reaction with cyclopentanone only produced monoaminoformylated derivatives. The corresponding meso-bromo derivatives can be obtained by using phosphorus bromide in place of the oxychloride as shown by A. I. Ponogaev and S. M. Makin in "Meso-bromosubstituted Tricarbocyanines with Cyclic Fragments in the Conjugation Chain", Zh. Org. Khim. 17, 167 (1980). These methods were applied successfully to 2-indanone by G. A. Reynolds and K. H. Drexhage, in "Stable Heptamethine Pyrylium Dyes that Absorb in the Infrared", J. Org. Chem, 42, 885 (1977) and by G. M. Sosnovskii, A. P. Lugovskii, and I. G. Tishchenko in "Synthesis of Meso-substituted Tricarbocyanine Dyes with an Ortho-phenylene Bridge in the Chromophore", Zh. Org. Khim. 19, 2143 (1983). Also, in the later article, methods are described for the introduction of a phenyl substituent in the meso-position or the substituted cyclic glutaconaldehyde intermediates: the cycloalkanones are reacted with PhMgBr or PhLi yielding the corresponding alcohols which can be easily dehydrated; these intermediates are subjected to a two-step aminoformylation, first with dimethylformamide dimethyl acetal and then with the DMF-POCl$_3$ complex. Functionalised side arms can be introduced in the para position of the phenyl substituent, by masking the functionality with appropriate protective groups, i.e. dioxanes or dioxolanes for aldehydes, oxazolines for carboxylic groups and tetrahydropyranes for alcohols, as described in the book by T. W. Greene and P. G. M. Wuts, "Protective Groups in Organic Synthesis", John Wiley & Sons, New York, N.Y. (1991).

Trimethincyanines with a meso chloro groups are best made as disclosed by G. L. Oliver in "Photographic Emulsions and $\mu$-chlorocarbocyanine Dyes", U.S. Pat. No. 3,656,960 (1962).

In trimethincyanines and heptamethine cyanines the meso halogen is easily displaceable by more nucleophilic atoms such as O, S, Se, and N. This provides a convenient route for the introduction of a great number of functionalised side arms, by using reagents bearing a functional group at their distal end. As was shown above, this method found some very limited application by Patonay and his group, in the preparation of heptamethincyanines with an isothiocyanate reactive group at the distal end of a thiophenyl meso substituent. This reagent has only very limited utility, mostly for cell or protein labelling, while it is totally unsuitable for the labelling of small molecules such as nucleotides. It is the purpose of this invention to provide better compounds by this route for applications where it is important to limit the perturbation caused to much the labelled molecule.

The above method could not be extended to pentamethincyanines, where the meso halogen not easily displaceable by nucleophiles. This effect is due to the alternation of charge density in the meso methine carbon in the series tri-, penta- and heptamethine dyes. In other words, the halogen-carbon bond in the meso position of pentamethincyanines is similar to that found in vinyl or aromatic halides. On this basis, it is possible to exploit the methods developed for the creation of carbon-carbon bonds from sp$^2$ halides and unsaturated hydrocarbons with the help of palladium catalysts, as described by R. F. Heck in "Palladium Reagents in Organic Synthesis", Academic Press, New York, N.Y., 1985; J. Tsuji, in "Palladium Reagents and Catalysts", John Wiley & Sons, New York, N.Y., 1995; and by J.-L. Malleron, J.-C-Fiaud, and J.-Y. Legros, in "Handbook of Palladium-Catalysed Organic Reactions", Academic Press, New York, N.Y., 1997. Especially useful in our context is the reaction between sp² halides and alkynes bearing a functional groups. These reactions are tolerant of many functionalities, occur under mild condition and in high yields. Similar methods proved successful also in the case of trimethine and heptamethincyanines, where the meso halogen is much more labile.

Other methods were developed for pentamethincyanines. In some cases, it is possible to synthesise pentamethine cyanines bearing useful functional groups in the meso position, for example an ester group, as disclosed by F. P. Doyle, in "Improvements in or Relating to the Production of Cyanine Dyestuffs and to the Sensitising of Photographic Emulsions", G.B. Patent No. 640,127 (1950). The Vilsmeyer-Haack-Arnold reaction is also very useful for the preparation of meso-substituted malondialdehydes needed for the preparation of the corresponding meso-substituted pentamethincyanines, C. M. Marson and P. R. Giles, "Synthesis Using Vilsmeier Reagents", CRC Press, Boca Raton, Fla., 1994. For example by treating substituted acetic acids, R—COOH, where R is aryl, chloro, ethoxycarbonyl, with an excess of the Vilsmeier reagent N,N.dimethylformamide-POCl$_3$ results in substituted malonaldialdehyde synthetic equivalents, $CH_3N^+=C-CR=CH-N(CH_3)_2$.

The subject-matter of the present invention is therefore constituted by symmetric cyanine labelling dyes having the general formula (1):

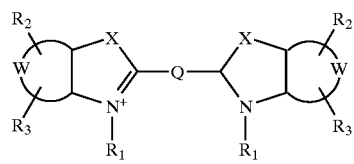

wherein:

X is selected from the group consisting of O, S and C(CH$_3$)$_2$;

W represents non-metal atoms required to form a benzo-condensed or a naphto-condensed ring;

R$_1$ is selected from the group consisting of (CH$_2$)$_n$CH$_3$, (CH$_2$)$_n$SO$_3^-$ and (CH$_2$)$_n$SO$_3$H, wherein n is an integer selected from 0 to 6 when R$_1$ is (CH$_2$)$_n$CH$_3$, and n is an integer selected from 3 to 6 when R$_1$ is (CH$_2$)$_n$SO$_3^-$ or (CH$_2$)$_n$SO$_3$H;

R$_2$ and R$_3$ are independently selected from the group consisting of H, a sulphonic moiety and a sulphonate moiety;

Q is selected from the group consisting of:

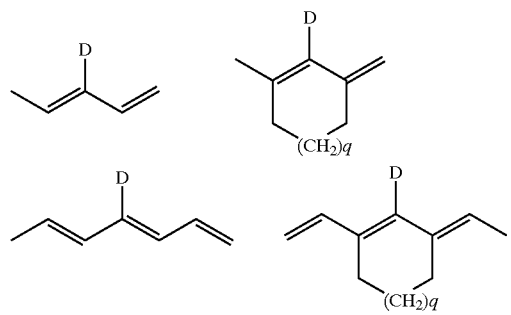

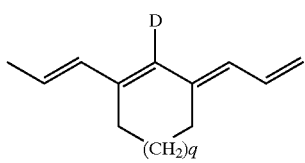

wherein q is 0 or 1 and D is selected from the group consisting of:

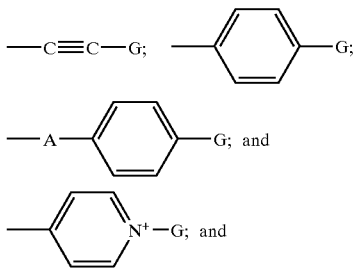

wherein A is O or S and G is, or contains a N, O or S nucleophile moiety or is, or contains a moiety capable of reacting with N, O or S nucleophiles.

It is understood that the case where q=0 refers to a ring having 5 carbon atoms.

Preferably, the N, O or S nucleophile moiety is selected from the group consisting of: (CH$_2$)$_m$OH, (CH$_2$)$_m$NH$_2$, (CH$_2$)$_m$SH, (CH$_2$)$_m$Y(CH$_2$)$_p$OH, (CH$_2$)$_m$Y(CH$_2$)$_p$NH$_2$, and (CH$_2$)$_m$Y(CH$_2$)$_p$SH.

Preferably, the moiety capable of reacting with N, O or S nucleophiles is selected from the group consisting of: (CH$_2$)$_m$COOH, (CH$_2$)$_m$glycidyl, (CH$_2$)$_m$maleimide, (CH$_2$)$_m$CO—NHS, (CH$_2$)$_m$CO-imidazole, (CH$_2$)$_m$SO$_2$CH=CH$_2$, (CH$_2$)$_m$CONHNH$_2$, (CH$_2$)$_m$CHO, (CH$_2$)$_m$Y(CH$_2$)$_p$COOH, (CH$_2$)$_m$Y(CH$_2$)$_p$glycidyl, (CH$_2$)$_m$Y(CH$_2$)$_p$maleimide, (CH$_2$)$_m$Y(CH$_2$)$_p$CO—NHS, (CH$_2$)$_m$Y(CH$_2$)$_p$CO-imidazole, CH$_2$(CH$_2$)$_m$O—PAM, (CH$_2$)$_m$Y(CH$_2$)$_p$SO$_2$CH=CH$_2$, (CH$_2$)$_m$Y(CH$_2$)$_p$CONHNH$_2$, (CH$_2$)$_m$Y(CH$_2$)$_p$CHO, and (CH$_2$)$_m$Y(CH$_2$)$_p$O—PAM, wherein

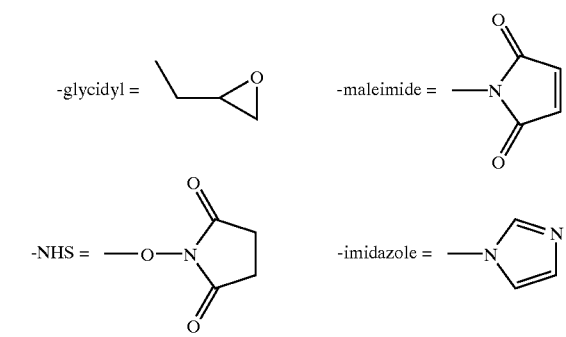

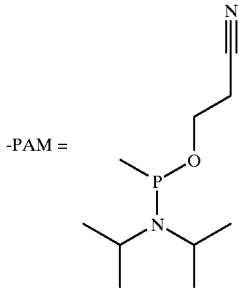

$$-PAM =$$

In the above formulae Y is selected from the group consisting of —NH—, —CONH—, —O— and —S—, m is an integer selected from 0 to 6 and p is an integer selected from 1 to 6.

In the above illustrated symmetric cyanines, it is preferred that at least one of the moieties $R_1$ to $R_3$ is, or contains a sulfonic or a sulphonate moiety.

In a preferred embodiment of the symmetric cyanines of the invention, X is $C(CH_3)_2$ and one of the moieties $R_2$ and $R_3$ is a sulphonic moiety or a sulphonate moiety; according to this embodiment of the invention, $R_1$ is more preferably $(CH_2)_nSO_3^-$ or $(CH_2)_nSO_3H$.

In another preferred embodiment of the symmetric cyanines of the invention, X is S and $R_1$ is $(CH_2)_nSO_3^-$ or $(CH_2)_nSO_3H$.

Also salts of the above illustrated symmetric cyanines are within the scope of the present invention. Examples of such salts include, but are not limited to, chloride, iodide and bromide salts; sodium, potassium and magnesium salts.

Also the valence tautomers of the symmetric cyanines of formula (1) are included within the scope of the invention, wherein the valence tautomerism is intended to mean the shifting of the conjugated bonds in the polymethine chain. Examples of symmetric cyanines of the present invention are compounds of formula (1) in which G, $R_1$, $R_2$, $R_3$ have the meanings illustrated in table 1 below.

TABLE 1

| G | $R_1$ | $R_2$ | $R_3$ |
|---|---|---|---|
| $(CH_2)_m$COOH | $(CH_2)_n$CH$_3$ | H | H |
| $(CH_2)_m$COOH | $(CH_2)_n$SO$_3$H | H | SO$_3$H |
| $(CH_2)_m$COOH | $(CH_2)_n$CH$_3$ | SO$_3$H | H |
| $(CH_2)_m$COOH | $(CH_2)_n$SO$_3$H | SO$_3$H | H |
| $(CH_2)_m$COOH | $(CH_2)_n$CH$_3$ | SO$_3$H | SO$_3$H |
| $(CH_2)_m$COOH | $(CH_2)_n$SO$_3$H | SO$_3$H | SO$_3$H |
| $(CH_2)_m$OH | $(CH_2)_n$CH$_3$ | H | H |
| $(CH_2)_m$OH | $(CH_2)_n$SO$_3$H | H | SO$_3$H |
| $(CH_2)_m$OH | $(CH_2)_n$CH$_3$ | SO$_3$H | H |
| $(CH_2)_m$OH | $(CH_2)_n$SO$_3$H | SO$_3$H | H |
| $(CH_2)_m$OH | $(CH_2)_n$CH$_3$ | SO$_3$H | SO$_3$H |
| $(CH_2)_m$OH | $(CH_2)_n$SO$_3$H | SO$_3$H | SO$_3$H |
| $(CH_2)_m$NH$_2$ | $(CH_2)_n$CH$_3$ | H | H |
| $(CH_2)_m$NH$_2$ | $(CH_2)_n$SO$_3$H | H | SO$_3$H |
| $(CH_2)_m$NH$_2$ | $(CH_2)_n$CH$_3$ | SO$_3$H | H |
| $(CH_2)_m$NH$_2$ | $(CH_2)_n$SO$_3$H | SO$_3$H | H |
| $(CH_2)_m$NH$_2$ | $(CH_2)_n$CH$_3$ | SO$_3$H | SO$_3$H |
| $(CH_2)_m$NH$_2$ | $(CH_2)_n$SO$_3$H | SO$_3$H | SO$_3$H |
| $(CH_2)_m$SH | $(CH_2)_n$CH$_3$ | H | H |
| $(CH_2)_m$SH | $(CH_2)_n$SO$_3$H | H | SO$_3$H |
| $(CH_2)_m$SH | $(CH_2)_n$CH$_3$ | SO$_3$H | H |
| $(CH_2)_m$SH | $(CH_2)_n$SO$_3$H | SO$_3$H | H |
| $(CH_2)_m$SH | $(CH_2)_n$CH$_3$ | SO$_3$H | SO$_3$H |
| $(CH_2)_m$SH | $(CH_2)_n$SO$_3$H | SO$_3$H | SO$_3$H |
| $(CH_2)_m$glycidyl | $(CH_2)_n$CH$_3$ | H | H |
| $(CH_2)_m$glycidyl | $(CH_2)_n$SO$_3$H | H | SO$_3$H |
| $(CH_2)_m$glycidyl | $(CH_2)_n$CH$_3$ | SO$_3$H | H |
| $(CH_2)_m$glycidyl | $(CH_2)_n$SO$_3$H | SO$_3$H | H |
| $(CH_2)_m$glycidyl | $(CH_2)_n$CH$_3$ | SO$_3$H | SO$_3$H |

TABLE 1-continued

| G | $R_1$ | $R_2$ | $R_3$ |
|---|---|---|---|
| $(CH_2)_m$glycidyl | $(CH_2)_n$SO$_3$H | SO$_3$H | SO$_3$H |
| $(CH_2)_m$maleimide | $(CH_2)_n$CH$_3$ | H | H |
| $(CH_2)_m$maleimide | $(CH_2)_n$SO$_3$H | H | SO$_3$H |
| $(CH_2)_m$maleimide | $(CH_2)_n$CH$_3$ | SO$_3$H | H |
| $(CH_2)_m$maleimide | $(CH_2)_n$SO$_3$H | SO$_3$H | H |
| $(CH_2)_m$maleimide | $(CH_2)_n$CH$_3$ | SO$_3$H | SO$_3$H |
| $(CH_2)_m$maleimide | $(CH_2)_n$SO$_3$H | SO$_3$H | SO$_3$H |
| $(CH_2)_m$CO-NHS | $(CH_2)_n$CH$_3$ | H | H |
| $(CH_2)_m$CO-NHS | $(CH_2)_n$SO$_3$H | H | SO$_3$H |
| $(CH_2)_m$CO-NHS | $(CH_2)_n$CH$_3$ | SO$_3$H | H |
| $(CH_2)_m$CO-NHS | $(CH_2)_n$SO$_3$H | SO$_3$H | H |
| $(CH_2)_m$CO-NHS | $(CH_2)_n$CH$_3$ | SO$_3$H | SO$_3$H |
| $(CH_2)_m$CO-NHS | $(CH_2)_n$SO$_3$H | SO$_3$H | SO$_3$H |
| $(CH_2)_m$CO-imidazole | $(CH_2)_n$CH$_3$ | H | H |
| $(CH_2)_m$CO-imidazole | $(CH_2)_n$SO$_3$H | H | SO$_3$H |
| $(CH_2)_m$CO-imidazole | $(CH_2)_n$CH$_3$ | SO$_3$H | H |
| $(CH_2)_m$CO-imidazole | $(CH_2)_n$SO$_3$H | SO$_3$H | H |
| $(CH_2)_m$CO-imidazole | $(CH_2)_n$CH$_3$ | SO$_3$H | SO$_3$H |
| $(CH_2)_m$CO-imidazole | $(CH_2)_n$SO$_3$H | SO$_3$H | SO$_3$H |
| $(CH_2)_m$SO$_2$CH=CH$_2$ | $(CH_2)_n$CH$_3$ | H | H |
| $(CH_2)_m$SO$_2$CH=CH$_2$ | $(CH_2)_n$SO$_3$H | H | SO$_3$H |
| $(CH_2)_m$SO$_2$CH=CH$_2$ | $(CH_2)_n$CH$_3$ | SO$_3$H | H |
| $(CH_2)_m$SO$_2$CH=CH$_2$ | $(CH_2)_n$SO$_3$H | SO$_3$H | H |
| $(CH_2)_m$SO$_2$CH=CH$_2$ | $(CH_2)_n$CH$_3$ | SO$_3$H | SO$_3$H |
| $(CH_2)_m$SO$_2$CH=CH$_2$ | $(CH_2)_n$SO$_3$H | SO$_3$H | SO$_3$H |
| $(CH_2)_m$CONHNH$_2$ | $(CH_2)_n$CH$_3$ | H | H |
| $(CH_2)_m$CONHNH$_2$ | $(CH_2)_n$SO$_3$H | H | SO$_3$H |
| $(CH_2)_m$CONHNH$_2$ | $(CH_2)_n$CH$_3$ | SO$_3$H | H |
| $(CH_2)_m$CONHNH$_2$ | $(CH_2)_n$SO$_3$H | SO$_3$H | H |
| $(CH_2)_m$CONHNH$_2$ | $(CH_2)_n$CH$_3$ | SO$_3$H | SO$_3$H |
| $(CH_2)_m$CONHNH$_2$ | $(CH_2)_n$SO$_3$H | SO$_3$H | SO$_3$H |
| $(CH_2)_m$CHO | $(CH_2)_n$CH$_3$ | H | H |
| $(CH_2)_m$CHO | $(CH_2)_n$SO$_3$H | H | SO$_3$H |
| $(CH_2)_m$CHO | $(CH_2)_n$CH$_3$ | SO$_3$H | H |
| $(CH_2)_m$CHO | $(CH_2)_n$SO$_3$H | SO$_3$H | H |
| $(CH_2)_m$CHO | $(CH_2)_n$CH$_3$ | SO$_3$H | SO$_3$H |
| $(CH_2)_m$CHO | $(CH_2)_n$SO$_3$H | SO$_3$H | SO$_3$H |
| $(CH_2)_m$Y$(CH_2)_p$COOH | $(CH_2)_n$CH$_3$ | H | H |
| $(CH_2)_m$Y$(CH_2)_p$COOH | $(CH_2)_n$SO$_3$H | H | SO$_3$H |
| $(CH_2)_m$Y$(CH_2)_p$COOH | $(CH_2)_n$CH$_3$ | SO$_3$H | H |
| $(CH_2)_m$Y$(CH_2)_p$COOH | $(CH_2)_n$SO$_3$H | SO$_3$H | H |
| $(CH_2)_m$Y$(CH_2)_p$COOH | $(CH_2)_n$CH$_3$ | SO$_3$H | SO$_3$H |
| $(CH_2)_m$Y$(CH_2)_p$COOH | $(CH_2)_n$SO$_3$H | SO$_3$H | SO$_3$H |
| $(CH_2)_m$Y$(CH_2)_p$CO-NHS | $(CH_2)_n$CH$_3$ | H | H |
| $(CH_2)_m$Y$(CH_2)_p$CO-NHS | $(CH_2)_n$SO$_3$H | H | SO$_3$H |
| $(CH_2)_m$Y$(CH_2)_p$CO-NHS | $(CH_2)_n$CH$_3$ | SO$_3$H | H |
| $(CH_2)_m$Y$(CH_2)_p$CO-NHS | $(CH_2)_n$SO$_3$H | SO$_3$H | H |
| $(CH_2)_m$Y$(CH_2)_p$CO-NHS | $(CH_2)_n$CH$_3$ | SO$_3$H | SO$_3$H |
| $(CH_2)_m$Y$(CH_2)_p$CO-NHS | $(CH_2)_n$SO$_3$H | SO$_3$H | SO$_3$H |
| $(CH_2)_m$Y$(CH_2)_p$CO-imidazole | $(CH_2)_n$CH$_3$ | H | H |
| $(CH_2)_m$Y$(CH_2)_p$CO-imidazole | $(CH_2)_n$SO$_3$H | H | SO$_3$H |
| $(CH_2)_m$Y$(CH_2)_p$CO-imidazole | $(CH_2)_n$CH$_3$ | SO$_3$H | H |
| $(CH_2)_m$Y$(CH_2)_p$CO-imidazole | $(CH_2)_n$SO$_3$H | SO$_3$H | H |
| $(CH_2)_m$Y$(CH_2)_p$CO-imidazole | $(CH_2)_n$CH$_3$ | SO$_3$H | SO$_3$H |
| $(CH_2)_m$Y$(CH_2)_p$CO-imidazole | $(CH_2)_n$SO$_3$H | SO$_3$H | SO$_3$H |
| $CH_2(CH_2)_m$O-PAM | $(CH_2)_n$CH$_3$ | H | H |
| $CH_2(CH_2)_m$O-PAM | $(CH_2)_n$CH$_3$ | H | SO$_3$H |
| $CH_2(CH_2)_m$O-PAM | $(CH_2)_n$CH$_3$ | SO$_3$H | H |
| $CH_2(CH_2)_m$O-PAM | $(CH_2)_n$CH$_3$ | SO$_3$H | H |
| $CH_2(CH_2)_m$O-PAM | $(CH_2)_n$CH$_3$ | SO$_3$H | SO$_3$H |
| $CH_2(CH_2)_m$O-PAM | $(CH_2)_n$CH$_3$ | SO$_3$H | SO$_3$H |
| $(CH_2)_m$Y$(CH_2)_p$O-PAM | $(CH_2)_n$CH$_3$ | H | H |
| $(CH_2)_m$Y$(CH_2)_p$O-PAM | $(CH_2)_n$CH$_3$ | H | SO$_3$H |
| $(CH_2)_m$Y$(CH_2)_p$O-PAM | $(CH_2)_n$CH$_3$ | SO$_3$H | H |
| $(CH_2)_m$Y$(CH_2)_p$O-PAM | $(CH_2)_n$CH$_3$ | SO$_3$H | H |
| $(CH_2)_m$Y$(CH_2)_p$O-PAM | $(CH_2)_n$CH$_3$ | SO$_3$H | SO$_3$H |
| $(CH_2)_m$Y$(CH_2)_p$O-PAM | $(CH_2)_n$CH$_3$ | SO$_3$H | SO$_3$H |

Each sulphonic moiety in the above table may be replaced by a corresponding sulphonate moiety.

Preferred symmetric cyanines according to the present invention are represented by any of the formulae (2a) to (2l):

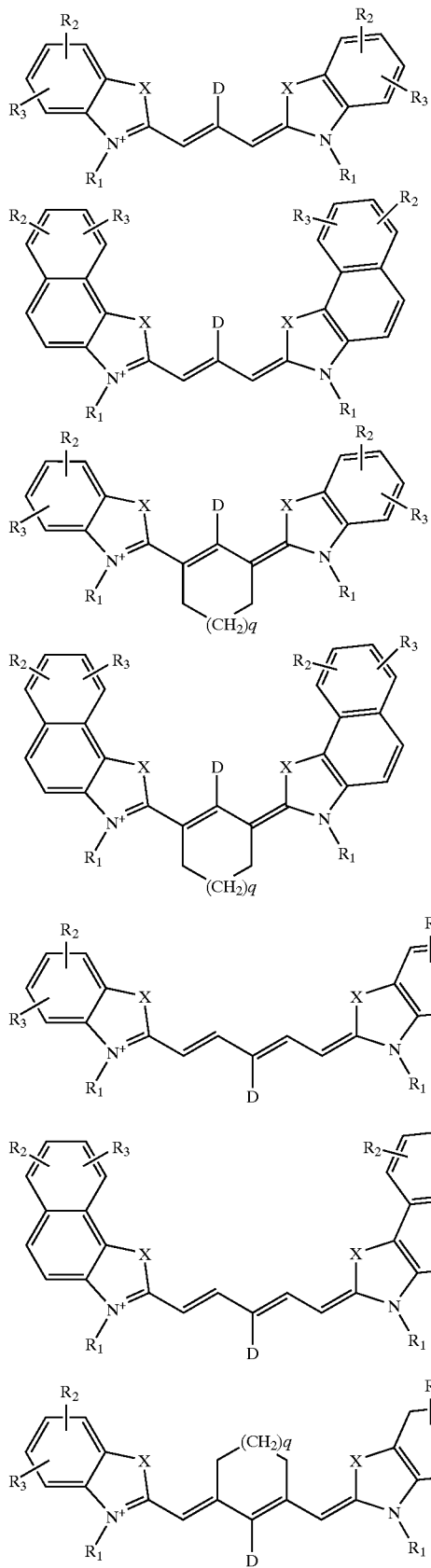

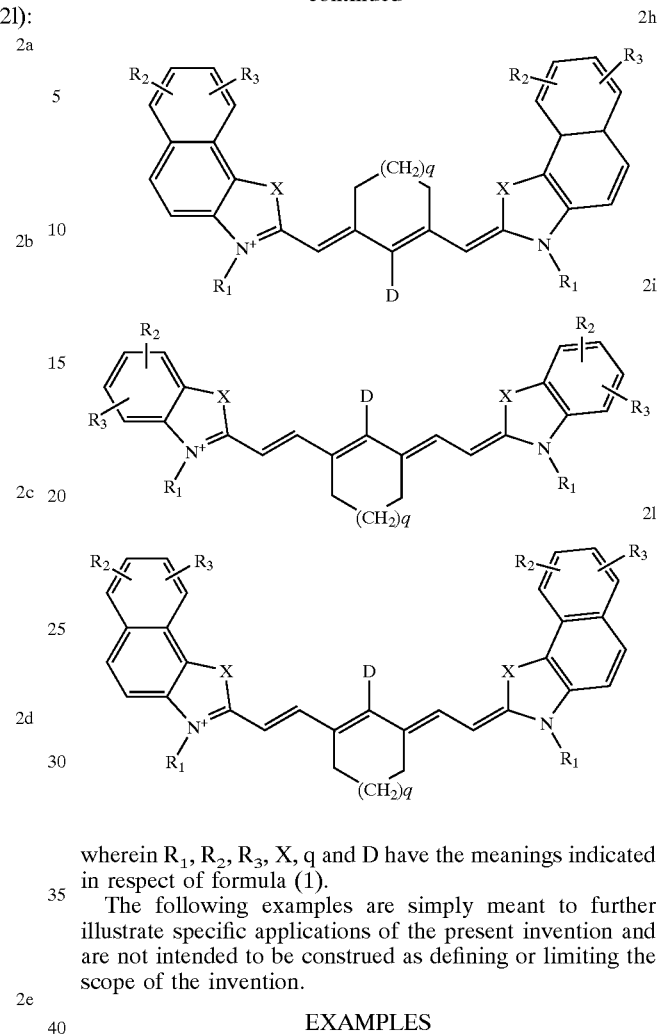

wherein $R_1$, $R_2$, $R_3$, X, q and D have the meanings indicated in respect of formula (1).

The following examples are simply meant to further illustrate specific applications of the present invention and are not intended to be construed as defining or limiting the scope of the invention.

EXAMPLES

Example 1

Synthesis of benzothiazolecarbo-µ-(2-carboxyethyl) cyanine iodide (Compound 1)

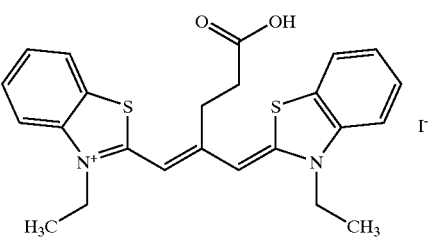

Compound 1

2.00 g of N-ethyl-2-methyl-benzothiazole, 5.25 g of succinic anhydride and 20 mL of pyridine are heated to reflux in a 100 mL flask for 30 minutes. After the reagents dissolve, the color of the solution turns to purple from yellow within 5 minutes. The solution is cooled to room temperature and added to a rapidly stirred solution of diethyl ether. The solid is collected on a filter funnel and then purified by flash chromatography on silica 60, 200–400 mesh, eluting with a dichloromethane/methanol 9/1 mixture. The purified product has $\lambda_{MeOH}$=548 nm.

Example 2

Synthesis of benzothiazolecarbo-μ-[3-hydroxy-(2-amidoethyl)]cyanine iodide and benzothiazolecarbo-μ-[3-amino-(2-amidoethyl)] cyanine iodide (Compounds 2a, 2b)

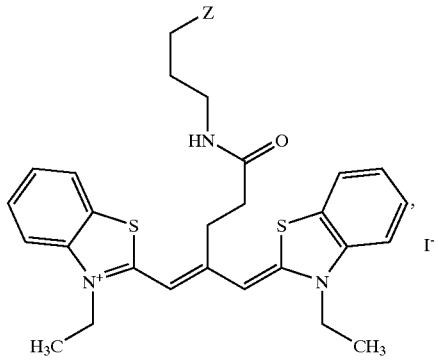

Compound 2a, Z = OH; Compound 2b, Z = NH$_2$

Compound 1 is dissolved in 1 mL of anhydrous N,N-dimethylformamide and equimolar amounts of dicyclohexylcarbodiimide and 1-hydroxybenzotriazole hydrate are added. After stirring for 5 minutes, a 5 fold excess of 1,3-aminopropanol is added. The reaction mixture is stirred overnight and then is added dropwise to 50 mL of rapidly stirred ether. The product is washed with ether and dried in a desiccator. 0.40 g of a fuchsia solid (compound 2a) are thus obtained, with $\lambda_{MeOH}$=550 nm. An amino-functionalised dye (compound 2b) is obtained by using an excess of 1,3-diaminopropane in place of 1,3-aminopropanol.

Example 3

Synthesis of benzothiazolecarbo-μ-[3-phosphoramidite-(2-amidoethyl)] cyanine iodide (Compound 3)

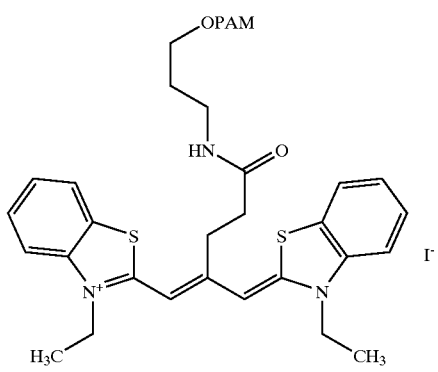

Compound 3

0.50 g of alcohol 2a is dried in a vacuum oven at 40° C. for five hours and then is loaded into a dry, 100 mL, 3-neck flask. 40 mL of anhydrous acetonitrile are added under argon, followed by 0.17 mL of a 0.5 M solution of tetrazole in acetonitrile and 0.42 mL of 2-cyanoethyltetraisopropylphosphorodiamidite. The solution is stirred under argon for 90 minutes at room temperature. After this time period it is evaporated in vacuo. The residue is re-dissolved in 1 mL of acetonitrile and precipitated by dropwise addition to 100 mL of anhydrous ether. It is stored at −20° C. The yield of 3 is 98%.

Example 4

Synthesis of n,n-bis(sulfobutyl)benzothiazolecarbo-μ-(2-carboxyethyl) cyanine sodium salt (Compound 4)

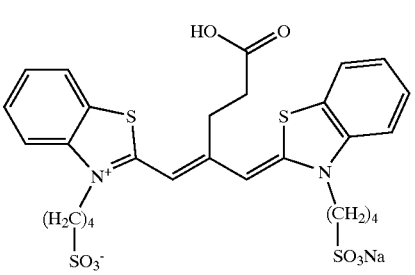

Compound 4

2.00 g of N-(δ-sulfonatobutyl)-2-methyl-benzothiazole, 5.25 g of succinic anhydride and 20 mL of pyridine are heated to reflux in a 100 mL flask for 30 minutes. After the reagent dissolve, the color of the solution turns to purple from yellow within 5 minutes. The solution is cooled to room temperature and added to a rapidly stirred solution of diethyl ether. The solid is collected on a filter funnel and then purified by reverse phase medium pressure chromatography on RP-18 LichroPrep (Merck), 25–40 μm. The product is eluted with a methanol/water 60/40 solvent mixture. The purified product has $\lambda_{MeOH}$=550 nm.

Example 5

Synthesis of n,n-bis(sulfobutyl)benzothiazolecarbo-μ-[4-carboxybutyl-(2-amidoethyl)] cyanine sodium salt (Compound 5)

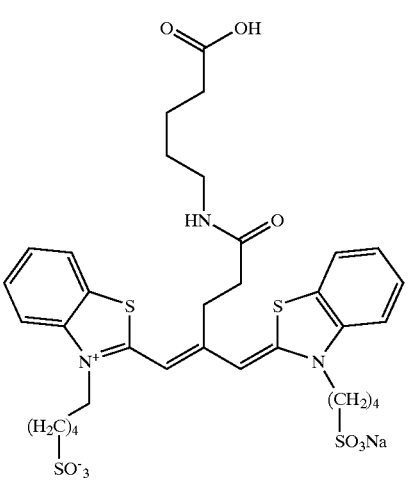

Compound 5

0.50 g of compound 4 is dissolved in 1 mL of anhydrous N,N-dimethylformamide and equimolar amounts of dicyclohexylcarbodiimide and 1-hydroxybenzotriazole hydrate are added. After stirring for 5 minutes, a 2 fold excess of 4-aminobutyric acid t-butyl ester is added. The reaction mixture is stirred overnight and then is added dropwise to 50 mL of rapidly stirred ether. The product is washed with ether and dried in a desiccator. The crude t-butyl ester is saponified by treatment with 1 mL of trifluoroacetic acid at room temperature. After 1 hour the trifluoroacetic acid is removed in vacuo to give a fuchsia solid. The crude product was purified by purified by reverse phase medium pressure chromatography on RP-18 LichroPrep (Merck), 25–40 µm. The product is eluted with a methanol/water 70/30 solvent mixture. The purified product, compound 5, has $\lambda_{MeOH}$=550 nm.

Example 6

Synthesis of n,n-bis(sulfobutyl)benzothiazolecarbo-µ-[4-succinimidyl ester butyl-(2-amidoethyl)] cyanine sodium salt (Compound 6)

Compound 6

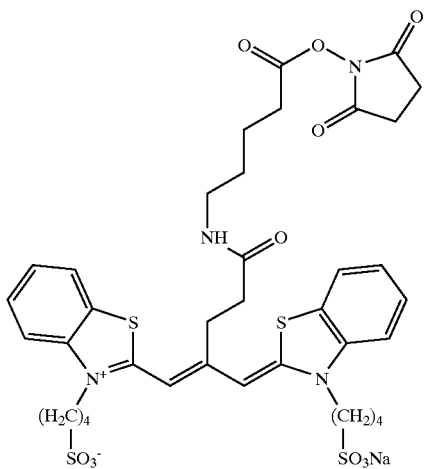

The acid 5 is converted to its N-hydroxysuccinimide ester as follows. 100 mg of the acid, and equimolar amounts of N,N'-dicyclohexylcarbodiimide and N-hydroxysuccinimide are dissolved in 3 mL of dry DMF in a microsynthesis vial. All glassware and reagents must be rigorously anhydrous. The solution is stirred overnight at 50° C. The active ester 6 is precipitated with anhydrous ether, collected on a glass filter and washed five times with anhydrous ether, dried and stored at −20° C. Yield of ester from the acid was 90%.

Example 7

Synthesis of bromomalonaldehyde dianil bromide (Compound 7)

Compound 7

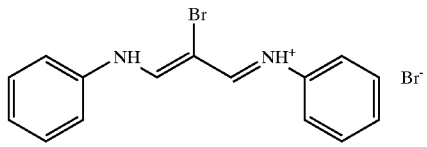

3.54 g of aniline are dissolved in 15 mL of ethanol in a 100 mL beaker. Separately, 5 g of muchobromic acid are dissolved in 15 mL of ethanol in a 100 mL Erlenmeyer flask. This solution is added drop by drop to the aniline/ethanol solution, with cooling. The reaction mixture turns immediately yellow, then orange, with development of $CO_2$. At the end of the addition, the mixture is heated in a water bath until its volume is reduced to one half. The resulting solution is cooled with an ice-salt mixture. A yellow crystalline mass is formed. This is collected on a fritted glass filter. A first fraction of 3.84 of pure product is obtained, 52% yield. From the mother solution a further 2.7 g of somewhat less pure product is recovered, which can be re-crystallised from a small amount of ethanol to yield a further 1.7 g of pure product.

Example 8

Synthesis of sulfoindodicarbo-µ-(bromo) cyanine iodide (Compound 8)

Compound 8

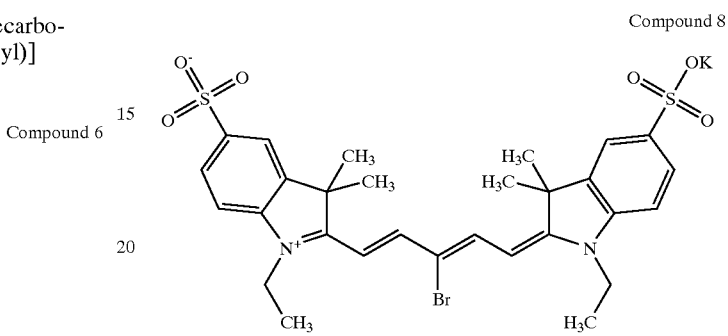

4 g of N-ethyl-2,3,3-trimethyl-3[H]indolium 5-sulphonate, 2.86 g of compound 7, 1.87 g of pyridine and 40 mL of acetic anhydride in a 100 mL flask are heated at reflux with stirring for 2 hours. The blue solution is cooled to room temperature and added dropwise to 400 mL of rapidly stirred diethyl ether. The blue-greenish solid is collected on a fritted glass filter, washed with ether and dried in a desiccator. The crude product is purified by reverse phase medium pressure chromatography on RP-18 Lichro-Prep (Merck), 25–40 µm. The product is eluted with a methanol/water 70/30 solvent mixture. Yield: 65%. The purified product has $\lambda_{MeOH}$=651 nm.

Example 9

Synthesis of sulfoindodicarbo-µ-(4-carboxy-1-butinyl) cyanine iodide (Compound 9)

Compound 9

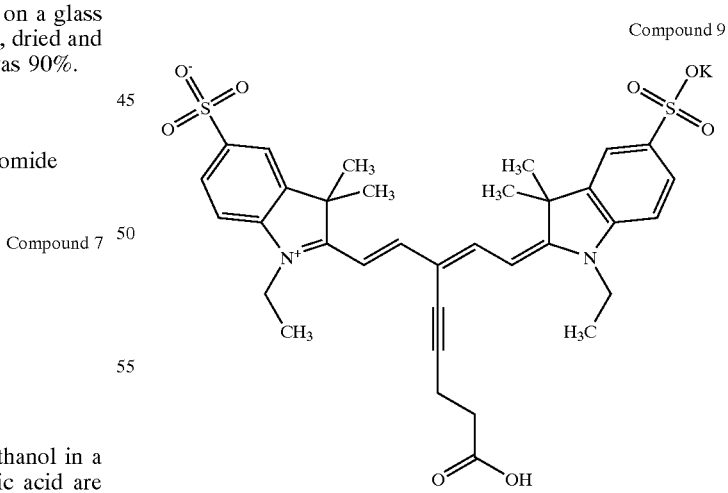

2 g of compound 8, 300 mg of 4-pentynoic acid and 1 mL of pyrrolidine are stirred into 15 mL of N,N-dimethylformamide under nitrogen at room temperature. 200 mg of bis(triphenylphosphine)-palladium(II) chloride, and 50 mg of cooper(I) iodide are added to the reaction mixture. After 4 hours, the solvent and volatile compounds are evaporated under vacuum. The crude product is purified by reverse phase medium pressure chromatography on RP-18 LichroPrep (Merck), 25–40 µm. The product is eluted with a methanol/water 70/30 solvent mixture. Yield: 65%. The purified product has $\lambda_{MeOH}$=655 nm

Example 10

Synthesis of sulfoindodicarbo-µ-(4-succinimidyl ester-1-butinyl) cyanine potassium salt (Compound 10)

Compound 10

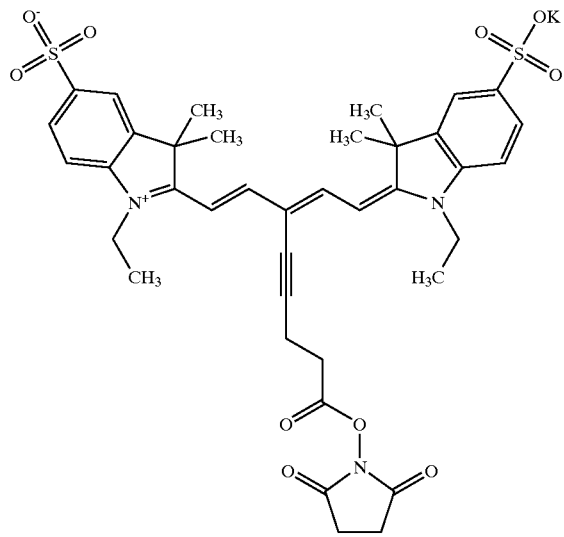

The acid 9 is converted to its N-hydroxysuccinimide ester as follows. 300 mg of the acid, and equimolar amounts of N,N'-dicyclohexylcarbodiimide and N-hydroxysuccinimide are dissolved in 10 mL of dry DMF in a microsynthesis vial. All glassware and reagents must be rigorously anhydrous. The solution is stirred overnight at 50° C. The active ester 10 is precipitated with anhydrous ether, collected on a glass filter and washed five times with anhydrous ether, dried and stored at −20° C. Yield of ester from the acid was 90%.

Example 11

Synthesis of indodicarbo-µ-(bromo) cyanine iodide (Compound 11)

Compound 11

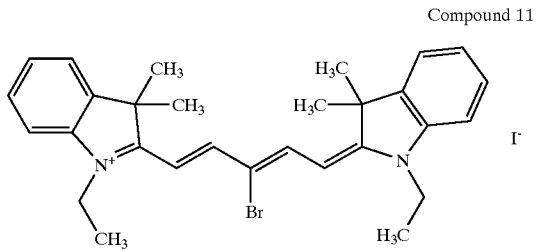

4.4 g of N-ethyl-2,3,3-trimethyl-3[H]indolium iodide, 2.86 g of compound 7, 1.87 g of pyridine and 40 mL of acetic anhydride in a 100 mL flask are heated at reflux with stirring for 2 hours. The blue solution is cooled to room temperature and added dropwise to 400 mL of rapidly stirred diethyl ether. The blue solid is collected on a synthered glass filter, washed with ether and deride in a desiccator. The product was purified by flash chromatography on silica 60, 200–400 mesh, eluting with a dichloromethane/methanol 95/5 mixture The purified product has $\lambda_{MeOH}$=644 nm

Example 12

Synthesis of indodicarbo-µ-(4-carboxy-1-butinyl) cyanine iodide (Compound 12)

Compound 12

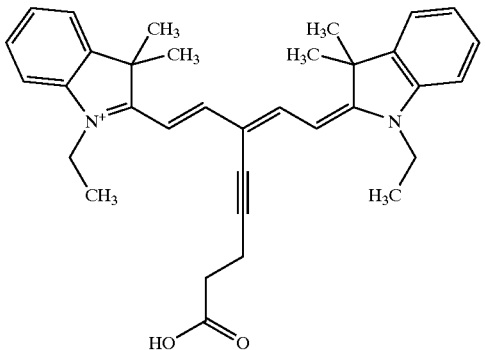

2 g of compound 11, 300 mg of 4-pentynoic acid and 1 mL of pyrrolidine are stirred into 15 mL of N,N-dimethylformamide under nitrogen at room temperature. 200 mg of bis(triphenylphosphine)-palladium(II) chloride, and 50 mg of cooper(I) iodide are added to the reaction mixture. After 4 hours, the solvent and volatile compounds are evaporated under vacuum. The crude product is purified by flash chromatography on silica 60, 200–400 mesh, eluting with a dichloromethane/methanol 9/1 mixture. Yield: 90%. The purified product has $\lambda_{MeOH}$=645 nm.

Example 13

Synthesis of indodicarbo-µ-[4-(3-hydroxypropylamido)-1-butinyl] cyanine iodide and indodicarbo-µ-[4-(3-aminopropylamido)-1-butinyl] cyanine iodide (Compounds 13a, 13b)

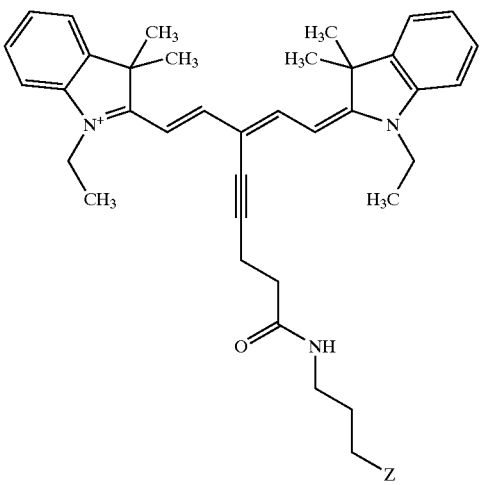

Compound 13a, Z = OH; Compound 13b, Z = NH₂

0.50 g of compound 12 is dissolved in 1 mL of anhydrous N,N-dimethylformamide and equimolar amounts of dicyclohexylcarbodiimide and 1-hydroxybenzotriazole hydrate are added. After stirring for 5 minutes, a 5 fold excess of 1,3-aminopropanol is added. The reaction mixture is stirred overnight and then is added dropwise to 50 mL of rapidly stirred ether. The product is washed with ether and dried in a desiccator. 0.40 g of a blue solid (compound 13a) are thus obtained, with $\lambda_{MeOH}$=648 nm. An amino-functionalised dye (compound 13b) is obtained by using an excess of 1,3-diaminopropane in place of 1,3-aminopropanol.

Example 14

Synthesis of indodicarbo-μ-[4-(3-phopsphoramidite propylamido)-1-butinyl] cyanine iodide (Compound 14)

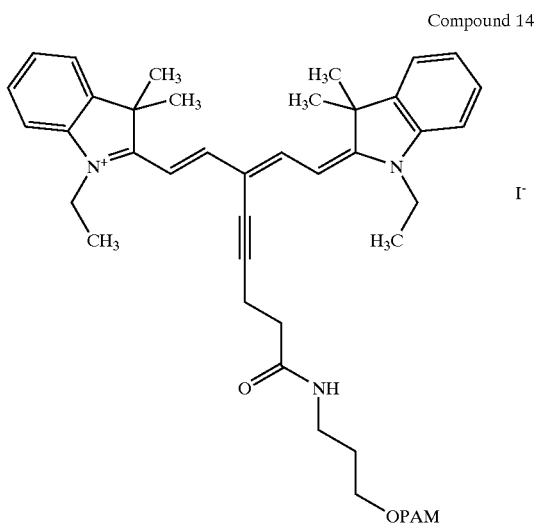

Compound 14

0.50 g of alcohol 13 is dried in a vacuum oven at 40° C. for five hours and then is loaded into a dry, 100 mL, 3-neck flask. 40 mL of anhydrous acetonitrile are added under argon, followed by 0.17 mL of a 0.5 M solution of tetrazole in acetonitrile and 0.42 mL of 2-cyanoethyltetraisopropylphosphorodiamidite. The solution is stirred under argon for 90 minutes at room temperature. After this time period it is evaporated in vacuo. The residue is re-dissolved in 1 mL of acetonitrile and precipitated by dropwise addition to 100 mL of anhydrous ether. It is stored at −20° C. The yield of 14 is 95%.

Example 15

Synthesis of p-carboxyphenylmalonaldehyde dianil chloride (Compound 15)

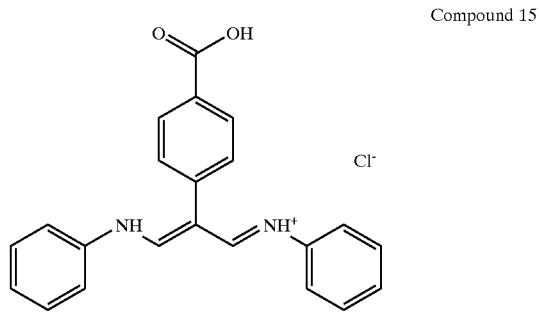

Compound 15

28 mL of POCl$_3$ are added to 39 mL stirred, cooled N,N-dimethylformamide, followed by 16 g of p-cyanophenylacetic. After 1 hour, the reaction mixture is heated at 80–90° C. until carbon dioxide is no longer evolved, about 6 hours. The mixture is cooled to room temperature, mixed within 100 g of ice, and the aqueous mixture is shaken with a small amount of charcoal. The aqueous solution is made basic with potassium carbonate and extracted 3 times with 200 mL portions of dichloromethane. The combined organic layers are washed with distilled water, dried with sodium sulphate and evaporated to a dark oil. This oil is subjected to basic hydrolysis to produce the free dihaldehyde and at the same time convert the nitrile to the corresponding carboxylate. Thus, the oil is suspended in 100 mL of water and 25 mL of 50% aqueous NaOH are added with stirring. The mixture is heated at 70° C. until a homogenous aqueous solution results. The solution is neutralised with concentrated hydrochloric acid and 25 g of aniline hydrochloride dissolved in 100 mL of water are added. The yellow orange precipitate is collected on a fritted glass filter and dried in the oven at 50° C.

Example 16

Synthesis of indodicarbo-μ-(4-carboxyphenyl) cyanine iodide (Compound 16)

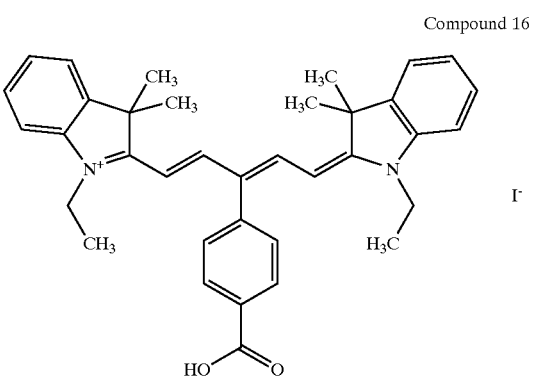

Compound 16

4.4 g of N-ethyl-2,3,3-trimethyl-3[H]indolium iodide, 2.64 g of compound 15, 2.00 g of pyridine and 50 mL of acetic anhydride in a 100 mL flask are heated at reflux with stirring for 2 hours. The blue solution is cooled to room temperature and added dropwise to 400 mL of rapidly stirred diethyl ether. The blue solid is collected on a fritted glass filter, washed with ether and dried in a desiccator. The product was purified by flash chromatography on silica 60, 200–400 mesh, eluting with a dichloromethane/methanol 95/5 mixture. The purified product has $\lambda_{MeOH}$=648 nm

Example 17

Synthesis of indodicarbo-μ-[4-(3-hydroxypropylamido)phenyl] cyanine iodide and indodicarbo-μ-[4-(3-aminopropylamido)-1-butinyl] cyanine iodide (Compounds 17a, 17b)

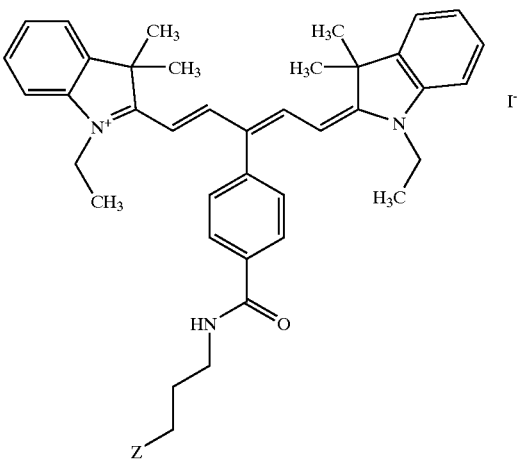

Compound 17a, Z = OH; Compound 17b, Z = NH$_2$ 0.50 g of compound 16 is dissolved in 1 mL of anhydrous N,N-dimethylformamide and equimolar amounts of dicyclohexylcarbodiimide and 1-hydroxybenzotriazole hydrate are added. After stirring for 5 minutes, a 5 fold excess of 1,3-aminopropanol is added. The reaction mixture is stirred overnight and then is added dropwise to 50 mL of rapidly stirred ether. The product is washed with ether and dried in a desiccator. 0.40 g of a blue solid (compound 17a) are thus obtained, with $\lambda_{MeOH}$=647 nm. An amino-functionalised dye (compound 17b) is obtained by using an excess of 1,3-diaminopropane in place of 1,3-aminopropanol.

Example 18

Synthesis of chloromalonaldehyde dianil chloride (Compound 18)

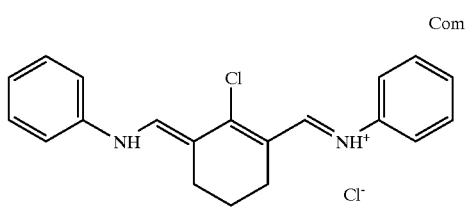

Compound 18

13 mL of anhydrous DMF are added under argon to a 250 mL flask fitted with a mechanical stirrer. 11 ml of $POCl_3$, previously cooled to 4° C. in the refrigerator, are slowly added drop by drop. The reaction mixture is cooled to 0° C. with a NaCl/ice bath under continuous stirring. A solution of 2.65 mL of cyclohexanone in 5 mL of dichloromethane is added dropwise. The color of the reaction mixture turn to yellow. At the of the addition, the mixture is stirred for a further 15 minutes and then heated on a water bath for 1 hour. It is then cooled to room temperature and a cold solution of 10 mL of aniline in 10 mL of ethanol is added dropwise. The reaction mixture turn to deep violet and becomes very viscous. 100 mL of cold water and 10 mL of cold concentrated HCl are added. The reaction mixture is transferred to a beaker, covered and kept in a refrigerator at 4° C. overnight. A dark violet crystalline mass precipitates and is collected on a fritted glass filter and washed several times with cold water. The product is dried overnight in a desiccator. The UV-Vis absorption spectrum shows two peaks, at 520 and 415 nm.

Example 19

Synthesis of 4-(2-carboxyethylamido)phenol, 4-(2-carboxypropylamido)phenol, 4-(2-carboxyethylamido)thiophenol and 4-(2-carboxypropylamido)thiophenol (Compounds 19a, 19b, 19c, 19d)

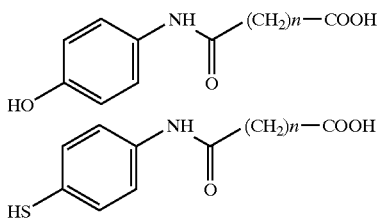

Phenols, Compound 19a n = 2; Compound 19b, n = 3
Thiophenols, Compound 19c n =2; Compound 19d, n = 3

11 g of p-aminophenol are suspended in 100 ml of water in a 500 mL flask, A suspension of 14 g of succinic anhydride in 100 mL of water is added with stirring. The mixture is warmed to 50° C. A crystalline mass precipitates. It is dissolved again by heating to the boil. The solution is cooled to room temperature. A white crystalline mass forms. This is collected on a fritted glass filter and washed with two portions of 50 mL of cold water and is dried in air. The yield of 19a is 86%. Compound 19b was similarly prepared from 11 g of p-aminophenol and 15 g of glutaric anhydride, yield 95%. The corresponding thiophenols (compounds 19c and 19d) were similarly prepared from 4-mercaptoaniline and succinic and glutaric anhydrides, respectively.

Example 20

Synthesis of indotricarbocyclohexen-$\mu$-(chloro) cyanine iodide (Compound 20)

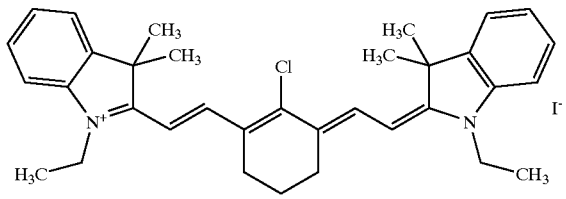

Compound 20

20 g of N-ethyl-2,3,3-trimethyl-3[H]indolium iodide, 11.4 g of compound 18, 6.3 g of sodium acetate anhydrous and 400 mL of ethanol are refluxed in a 1000 mL flask for 1 hour. The solution is cooled to room temperature and slowly added to 4 L of diethyl ether. The green precipitate is collected on a fritted glass filter and purified by flash chromatography on silica 60, 200–400 mesh, eluting with a dichloromethane/methanol 9/1 mixture.

Example 21

Synthesis of indotricarbocyclohexen-$\mu$-[3-(3-hydroxypropylamido)propylamidothiophenoxy] cyanine iodide and indotricarbocyclohexen-$\mu$-[3-(3-aminopropylamido)propylamidothiophenoxy] cyanine iodide (Compounds 21a, 21b)

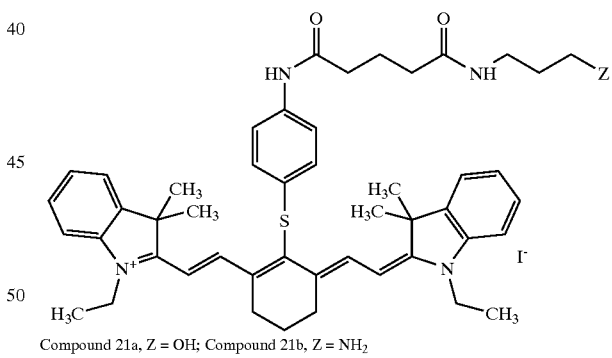

Compound 21a, Z = OH; Compound 21b, Z = NH$_2$

All the glassware is dried overnight at 120° C. Compounds 20 and 19d are dried in a vacuum oven for 90 minutes at 40° C. over silica gel. A 3-neck, 100 mL flask, cooled under a stream of nitrogen is loaded with 0.5 g of compound 20 and 1.72 g of compound 19d. 10 mL of anhydrous N,N-dimethylformamide are added by cannula under nitrogen. The mixture is stirred for 15 minutes under nitrogen. The solvent is evaporated and the residue dissolved in a small amount of methanol. The green methanol solution is filtered and added to 200 mL of rapidly stirred ether. The green precipitate is collected on a sintered glass filter and purified by purified by reverse phase medium pressure chromatography on RP-18 LichroPrep (Merck), 25–40 $\mu$m. The product is eluted with a methanol/water 70/30 solvent mixture. 0.40 g of an emerald green solid are thus obtained, with $\lambda_{MeOH}$=785 nm. The cyanine acid is dissolved in 1 mL of anhydrous N,N-dimethylformamide and equimolar amounts of dicyclohexylcarbodiimide and 1-hydroxybenzotriazole hydrate are added. After stirring for 5 minutes, a 5 fold excess of 1,3-aminopropanol is added. The reaction mixture is stirred overnight and then is added dropwise to 50 mL of rapidly stirred ether. The product is washed with ether and dried in a desiccator. 0.40 g of an emerald green solid (compound 21a) are thus obtained, with $\lambda_{MeOH}$=785. An amino-functionalised dye (compound 21b) is obtained by using an excess of 1,3-diaminopropane in place of 1,3-aminopropanol.

Example 22

Synthesis of indotricarbocyclohexen-$\mu$-[3-(3-phopsphoramidite propylamido) propylamido thiophenoxy] cyanine iodide (Compound 22)

Compound 22

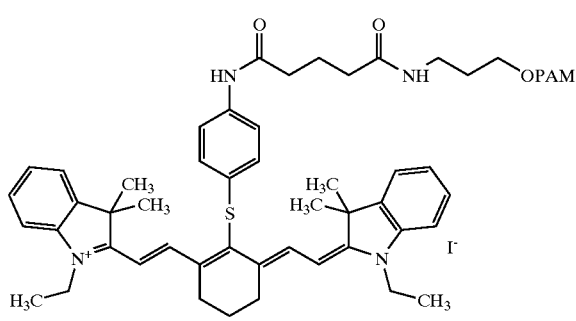

0.50 g of alcohol 21a is dried in a vacuum oven at 40° C. for five hours and then is loaded into a dry, 100 mL, 3-neck flask. 40 mL of anhydrous acetonitrile are added under argon, followed by 0.17 mL of a 0.5 M solution of tetrazole in acetonitrile and 0.42 ML of 2-cyanoethyltetraisopropylphosphorodiamidite. The solution is stirred under argon for 90 minutes at room temperature. After this time period it is evaporated in vacuo. The residue is re-dissolved in 1 mL of acetonitrile and precipitated by dropwise addition to 100 mL of anhydrous ether. It is stored at −20° C. The yield of 22 is 90%.

Example 23

Synthesis of sulfoindotricarbocyclohexen-$\mu$-(chloro) cyanine (Compound 23)

Compound 23

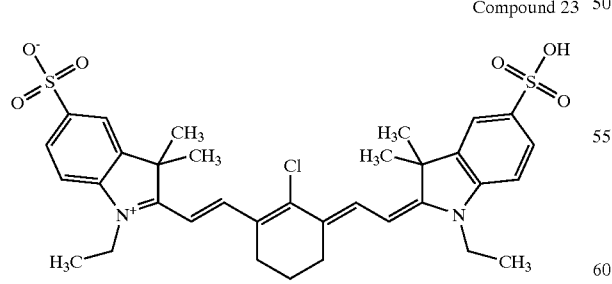

20 g of N-ethyl-2,3,3-trimethyl-3[H]-indolium-5-sulfonate, 13.5 g of compound 18, 6.10 g of sodium acetate anhydrous and 400 mL of ethanol are refluxed for 1 hour under stirring in a 1000 mL flask. The solution is cooled to room temperature and slowly added to 4 L of rapidly stirred diethyl ether. The green solid is collected on a filter and purified by reverse phase medium pressure chromatography on RP-18 LichroPrep (Merck), 25–40 $\mu$m. The product was eluted with a methanol/water 60/40 solvent mixture.

Example 24

Synthesis of sulfoindotricarbocyclohexen-$\mu$-[(3-carboxypropyl)amido]thiophenoxy cyanine sodium salt (Compound 24)

Compound 24

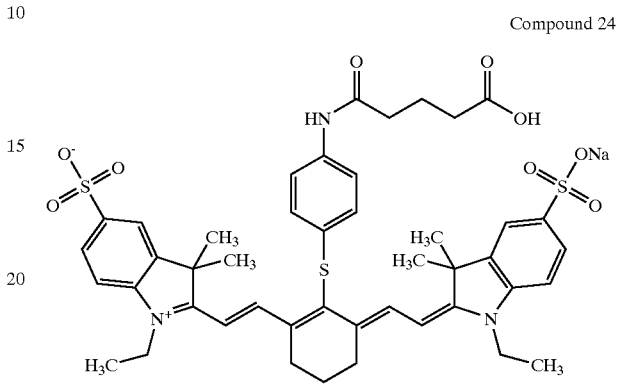

All the glassware is dried overnight at 120° C. Compounds 23 and 19d are dried in a vacuum oven for 90 minutes at 40° C. over silica gel. A 3-neck, 100 mL flask, cooled under a stream of nitrogen is loaded with 0.5 g of compound 23 and 1.72 g of compound 19d. 10 mL of anhydrous N,N-dimethylformamide are added by cannula under nitrogen. The mixture is stirred for 15 minutes under nitrogen. The solvent is evaporated and the residue dissolved in a small amount of methanol. The green methanol solution is filtered and added to 200 mL of rapidly stirred ether. The green precipitate is collected on a sintered glass filter and purified by purified by reverse phase medium pressure chromatography on RP-18 LichroPrep (Merck), 25–40 $\mu$m. The product is eluted with a methanol/water 70/30 solvent mixture. 0.55 g of a green solid are thus obtained, with $\lambda_{MeOH}$=794 nm.

Example 25

Synthesis of sulfoindotricarbocyclohexen-$\mu$-[(3-succinimidyl ester propyl)amido]thiophenoxy cyanine sodium salt (Compound 25)

Compound 25

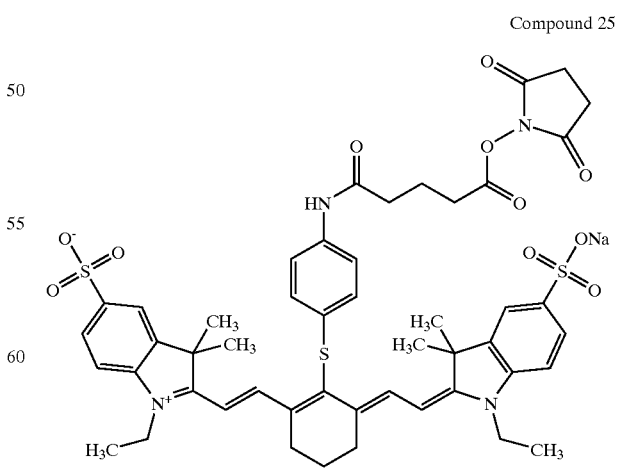

The acid 23 is converted to its N-hydroxysuccinimide ester as follows. 100 mg of the acid 24, and equimolar amounts of N,N'-dicyclohexylcarnodiimide and N-hydroxysuccinimide are dissolved in 3 mL of dry DMF in a microsynthesis vial. All glassware and reagents must be rigorously anhydrous. The solution is stirred overnight at 50° C. The active ester 25 is precipitated with anhydrous ether, collected on a glass filter and washed five times with anhydrous ether, dried and stored at −20° C. Yield of ester from the acid was 95%.

Example 26

Synthesis of the Conjugate Between Sulfoindotricarbocyclohexen-$\mu$-[(3-succinimidyl ester propyl)amido]thiophenoxy cyanine sodium salt and 5-allylamino-dUTP (Compound 26)

Compound 26

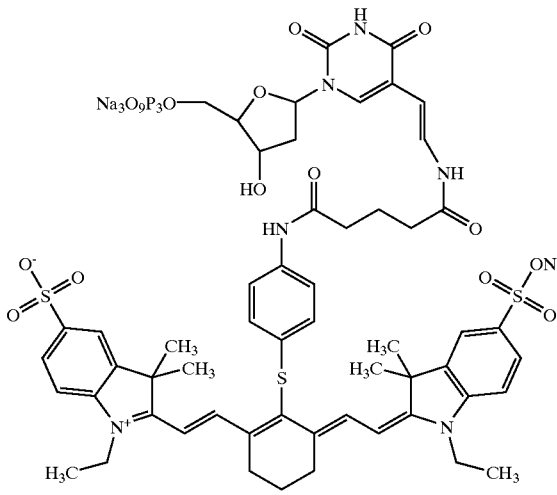

2 $\mu$mol of 5-allylamino-dUTP is dissolved in 1.2 mL 0.1 M borate buffer pH 8. 10 $\mu$mol of active ester 25 dissolved in 300 $\mu$mol of DMF are added to the 5-allylamino-dUTP solution and the mixture is stirred in the dark at room temperature. The reaction is monitored by RP-HPLC (column: Waters Novapack 3.9×150 mm; loop: 20 mL; flow rate: 1 mL/min; program: 15' linear gradient from 100% A to 50% A/50% B, 5' 50% A/50% B, 5' gradient back to 100 A %, with A=water with 0.1% trifluoroacetic acid and B=acetonitrile. The crude conjugate solution is prepurified by gel filtration chromatography on a 1.5×30 cm, Sephadex G-10 column, with water as eluent. The final purification is by medium pressure liquid chromatography on a Lichroprep RP-18, 20×300 column, with water/acetonitrile 70:30 as eluent. The coupling efficiency was 85%. The conjugate is stored at −20° C.

Example 27

Synthesis of 2-formyl-5-hydroxylyden-1-chlorocyclopenten (Compound 27)

Compound 27

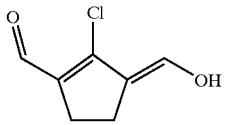

10 mL of anhydrous DMF and 10 mL of dichloromethane are added under argon to a 250 mL flask fitted with a mechanical stirrer. The mixture is cooled with a water/NaCl bath to 4–5° C. A solution of 9 ml of POCl$_3$ in 9 mL of dichloromethane previously cooled to 4° C. in the refrigerator, is slowly added drop by drop. The reaction mixture is cooled to 0° C. with a NaCl/ice bath under continuous stirring. The addition requires 45 minutes. The reaction mixture becomes milky and it is allowed to stand for 30 minutes at 4–5° C. A solution of 2.00 mL of cyclopentanone is added dropwise. The color of the reaction mixture turns to yellow. At the of the addition, the mixture is stirred for a further 15 minutes and then heated at reflux for 5 hours. Its color turns to orange and then to dark red. It is then cooled to room temperature. The dichloromethane solvent is evaporated in vacuo and the residue is thrown into 100 g of ice and is stirred for 2 hours. The pH of the solution is brought to 5 with 50% aqueous NaOH. A dark precipitate forms. The mixture is stirred overnight and the violet crystals are collected onto a fritted glass filter. Yield 2.46 g, 67%. The product, dissolved in methanol has a peak at 337 nm.

Example 28

Synthesis of benzo[e]indotricarbocyclopenten-$\mu$-(chloro) cyanine iodide (Compound 28)

Compound 28

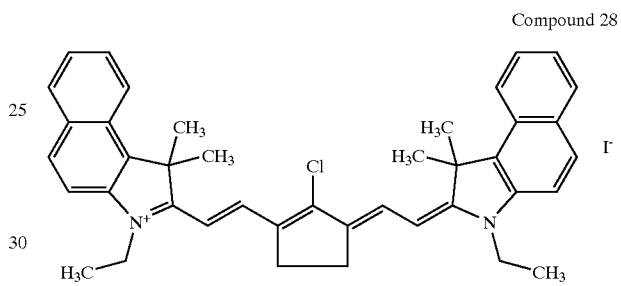

1.0 g of compound 3-ethyl-1,1,2-trimethyl-benz[e]-1[H] indolium iodide, 0.20 g of compound 27, 3 g of sodium acetate anhydrous and 10 mL are heated at reflux in a 3-neck, 50 mL flask for 30 minutes. The solution color turns to dark violet. The mixture is cooled to room temperature and is added dropwise to 500 mL of rapidly stirred ether and purified by flash chromatography on silica 60 200–400 mesh, eluting with a dichloromethane/methanol 9/1 mixture. Yield, 1.10 g. $\lambda_{MeOH}$=839 nm.

Example 29

Synthesis of benzo[e]indotricarbocyclopenten-$\mu$-[3-(3-hydroxypropylamido)propylamido]thiophenoxy cyanine iodide and benzo[e]indotricarbocyclopenten-$\mu$-[3-(3-aminopropylamido) propylamido]thiophenoxy cyanine iodide (Compounds 29a, 29b)

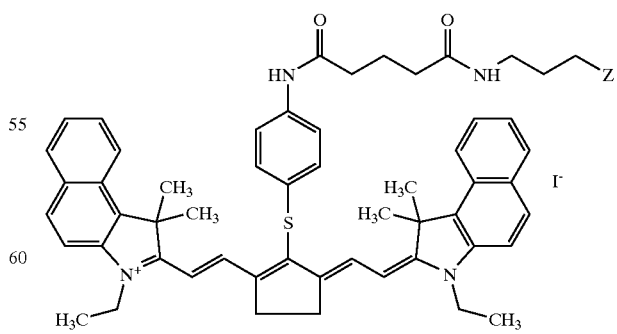

Compound 29a = OH; Compound 29b = NH$_2$

All the glassware is dried overnight at 120° C. Compounds 28 and 19d are dried in a vacuum oven for 90 minutes at 40° C. over silica gel. A 3-neck, 100 mL flask, cooled under a stream of nitrogen is loaded with 0.5 g of compound 28 and 2.0 g of compound 19d mL of anhydrous N,N-dimethylformamide are added by cannula under nitrogen. The mixture is stirred for 15 minutes under nitrogen. The solvent is evaporated and the residue dissolved in a small amount of methanol. The green methanol solution is filtered and added to 200 mL of rapidly stirred ether. The green precipitate is collected on a fritted glass filter and purified by purified by reverse phase medium pressure chromatography on RP-18 LichroPrep (Merck), 25–40 μm. The product is eluted with a methanol/water 70/30 solvent mixture. 0.40 g of an emerald green solid are thus obtained, with λMeOH=785 nm. The cyanine acid is dissolved in 1 mL of anhydrous N,N-dimethylformamide and equimolar amounts of dicyclohexylcrbodiimide and 1-hydroxybenzotriazole hydrate are added. After stirring for 5 minutes, a 5 fold excess of 1,3-aminopropanol is added. The reaction mixture is stirred overnight and then is added dropwise to 50 mL of rapidly stirred ether. The product is washed with ether and dried in a desiccator. 0.40 g of an emerald green solid (compound 29a) are thus obtained, with $\lambda_{MeOH}$=850 nm. An amino-functionalised dye (29b) compound is obtained by using an excess of 1,3-diaminopropane in place of 1,3-aminopropanol.

Example 30

Synthesis of benzo[e]indotricarbocyclopenten-μ-[3-(3-phosphoramidite propylamido)propylamido] thiophenoxy cyanine iodide (Compound 30)

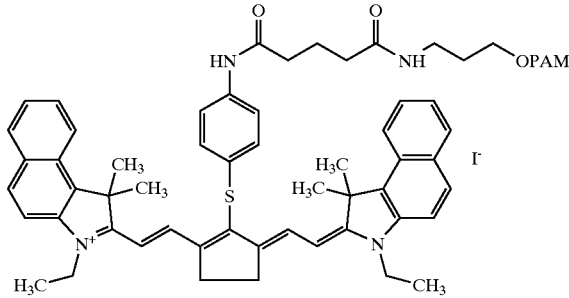

Compound 30

0.50 g of alcohol 29a is dried in a vacuum oven at 40° C. for five hours and then is loaded into a dry, 100 mL, 3-neck flask. 40 mL of anhydrous acetonitrile are added under argon, followed by 0.17 mL of a 0.5 M solution of tetrazole in acetonitrile and 0.42 mL of 2-cyanoethyltetraisopropylphosphorodiamidite. The solution is stirred under argon for 90 minutes at room temperature. After this time period it is evaporated in vacuo. The residue is re-dissolved in 1 mL of acetonitrile and precipitated by dropwise addition to 100 mL of anhydrous ether. It is stored at −20° C. The yield of 30 is 60%.

Example 31

Synthesis of 2-(4-pyridyl) malondialdehyde (Compound 31)

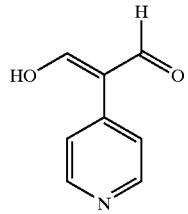

Compound 31

To 124 ml of N,N-dimethylformamide (DMF), stirred and cooled at +5° C. are added under argon 29.6 ml of POCl$_3$. The temperature is carried to room temperature and the mixture is stirred at this temperature for half an hour, then is cooled to −10° C. and 10.16 ml of picoline are added. The mixture is heated at 70° C. for 6 hours, then is cooled over night at room temperature and then mixed within 376 g of ice, stirred until the ice is melting.

The aqueous solution is subjected to basic hydrolysis to produce the free dihaldehyde. An aqueous solution of NaOH (64.4 g in 107 ml of water) is added dropwise. The mixture is stirred at room temperature for 2–3 hours, then is heated at 90° C. until a homogenous solution results and formation of basic vapours is finished.

The solution, after cooling in ice bath is neutralised with diluted HCl 1:1. The precipitate is collected on a fritted glass filter and dried in a desiccator.

Example 32

Synthesis of sulfoindodicarbo-μ-(4-pyridyl)cyanine sodium salt (Compound 32)

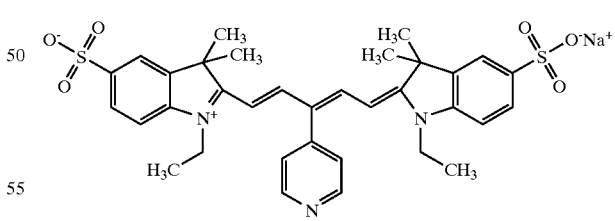

Compound 32

0.5 g of N-ethyl-2,3,3-trimethyl-3[H]indolium-5-sulfonate, 0.14 g of compound 31, 1 ml of dry pyridine and 20 ml of acetic anhydride in a 100 ml flask are heated at reflux for a hour. The blue solution is cooled to room temperature and added dropwise to 200 ml of rapidly stirred diethyl ether. The blue solid is collected on fritted glass filter, washed with ether and dried in a desiccator. The product has $\lambda_{MeOH}$=642 nm.

Example 33

Synthesis of sulfoindodicarbo-μ-[N-(5-carboxypenthyl)-4-pyridinium) cyanine (Compound 33)

Compound 33

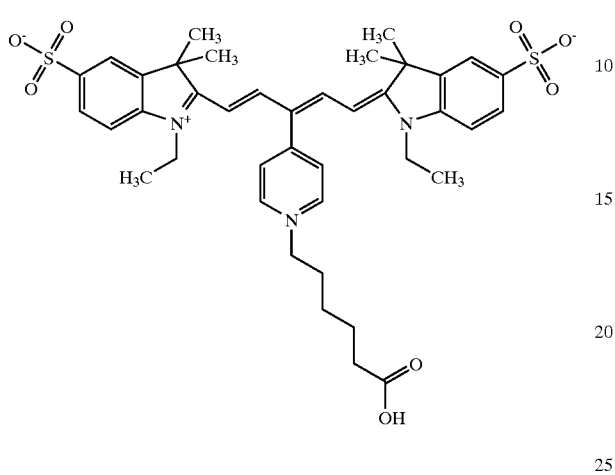

0.3 g of compound 32, 0.27 g of 6-bromohexanoic acid, 0.118 g of N-ethyldiisopropylamine and 20 ml of dry DMF in a 100 ml flask are heated, under argon, at 120° C. for 4 hours.

The blue solution is cooled to room temperature and added dropwise to 200 ml of rapidly stirred diethyl ether. The blue solid is collected on fritted glass filter, washed with ether and dried in a desiccator. The product has $\lambda_{MeOH}$=638 nm.

What is claimed is:

1. A symmetric cyanine of the formula:

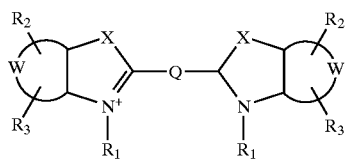

(1)

wherein:

X is $C(CH_3)_2$;

W represents non-metal atoms required to form a benzo-condensed or a naphto-condensed ring;

$R_1$ is selected from the group consisting of $(CH_2)_nCH_3$, $(CH_2)_nSO_3^-$ and $(CH_2)_nSO_3H$, wherein n is an integer selected from 0 to 6 when $R_1$ is $(CH_2)_nCH_3$, and n is an integer selected from 3 to 6 when $R_1$ is $(CH_2)_nSO_3^{31}$ or $(CH_2)_nSO_3H$;

$R_2$ and $R_3$ are independently selected from the group consisting of H, a sulphonic moiety and a sulphonate moiety;

Q is selected from the group consisting of:

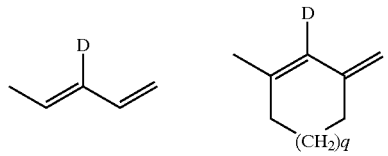

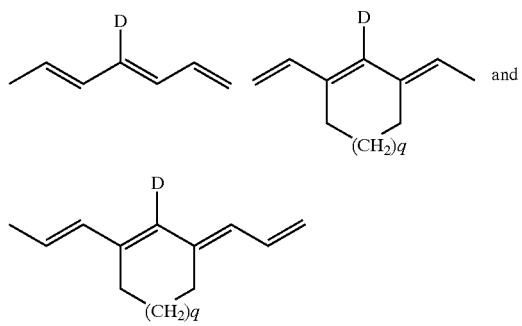

and wherein q is 0 or 1 and D is selected from the group consisting of:

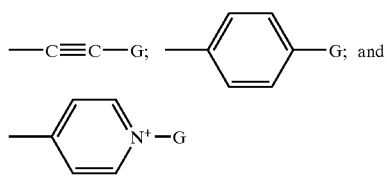

wherein

G is a nucleophile moiety selected from the group consisting of $(CH_2)_mNH_2$, $(CH_2)_mSH$, $(CH_2)_mY(CH_2)_pOH$, $(CH_2)_mY(CH_2)_pNH_2$ and $(CH_2)_mY(CH_2)_pSH$, wherein Y is selected from the group consisting of —NH—, —CONH—, —O— and —S—, m is an integer selected from 0 to 6 and p is an integer selected from 1 to 6;

or wherein G is a moiety capable of reacting with N, O or S nucleophiles, and is selected from the group consisting of $(CH_2)_mCOOH$, $(CH_2)_m$glycidyl, $(CH_2)_m$maleimide, $(CH_2)_mCO$—NHS, $(CH_2)_mCO$-imidazole, $(CH_2)_mSO_2CH$=$CH_2$, $(CH_2)_mCONHNH_2$, $(CH_2)_mCHO$, $(CH_2)_mY(CH_2)_pCOOH$, $(CH_2)_mY(CH_2)_p$glycidyl, $(CH_2)_mY(CH_2)_p$maleimide, $(CH_2)_mY(CH_2)_pCO$—NHS, $(CH_2)_mY(CH_2)_pCO$-imidazole, $CH_2(CH_2)_mO$—PAM, $(CH_2)_mY(CH_2)_pSO_2CH$=$CH_2$, $(CH_2)_mY(CH_2)_pCONHNH_2$, $(CH_2)_mY(CH_2)_pCHO$ and $(CH_2)_mY(CH_2)_pO$—PAM, wherein Y, m and p have the meanings indicated above.

2. A symmetric cyanine according to claim 1, wherein at least one of the moieties $R_1$ to $R_3$ is, or contains a sulphonic moiety or a sulphonate moiety.

3. A symmetric cyanine according to claim 1, wherein $R_1$ is $(CH_2)_nSO_3^-$ or $(CH_2)_nSO_3H$.

4. A symmetric cyanine according to claim 1 having any of the formulae 2a–2i or 2l:

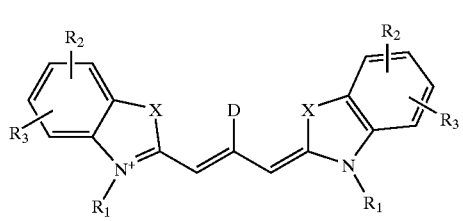

2a

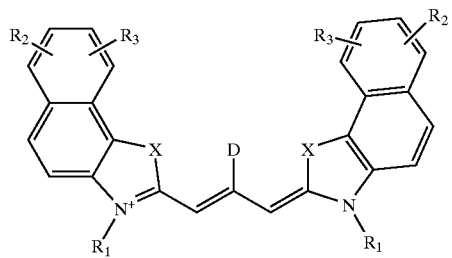
2b
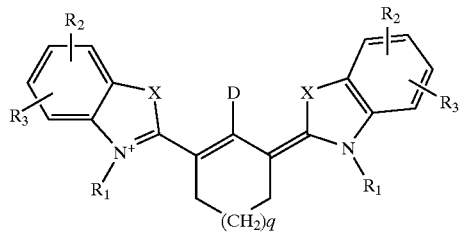
2c
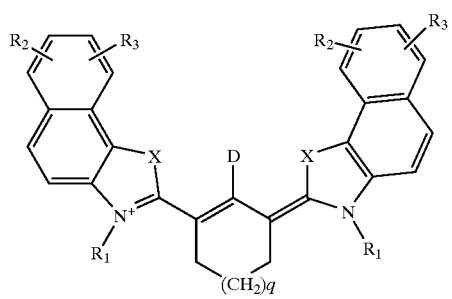
2d
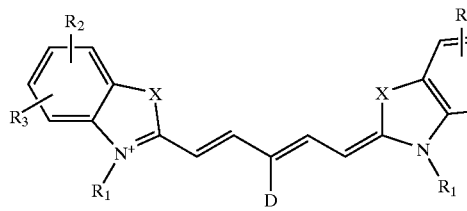
2e
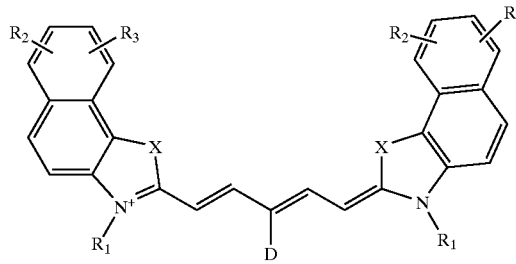
2f
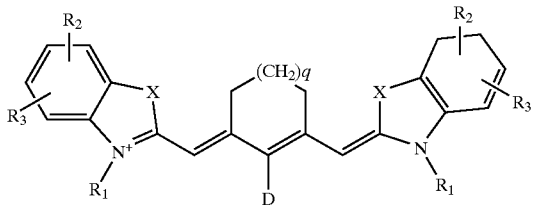
2g
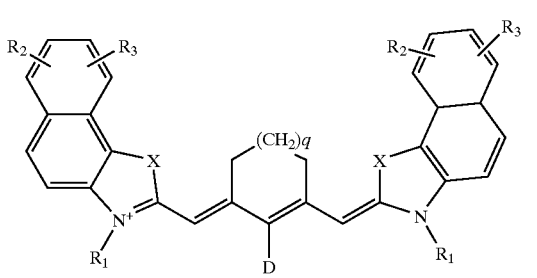
2h
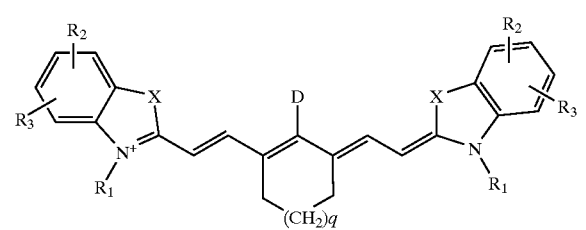
2i
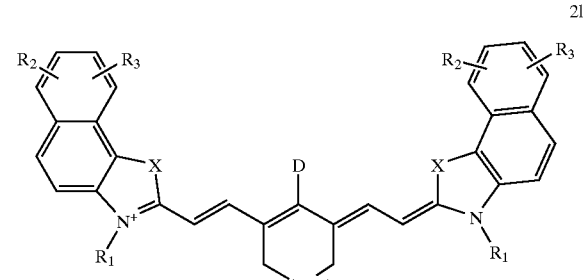
2l
wherein $R_1$, $R_2$, $R_3$, X, q and D have the meanings indicated in claim 1.
* * * * *